(12) United States Patent
Mito

(10) Patent No.: US 7,115,544 B2
(45) Date of Patent: Oct. 3, 2006

(54) PLANT GROWTH REGULATORS FOR COTTON HERVEST

(75) Inventor: Nobuaki Mito, Funabashi (JP)

(73) Assignee: Sumitomo Chemical Company, Limited, Osaka (JP)

( * ) Notice: Subject to any disclaimer, the term of this patent is extended or adjusted under 35 U.S.C. 154(b) by 291 days.

(21) Appl. No.: 10/476,511

(22) PCT Filed: May 31, 2001

(86) PCT No.: PCT/JP01/04584

§ 371 (c)(1),
(2), (4) Date: Nov. 3, 2003

(87) PCT Pub. No.: WO02/098227

PCT Pub. Date: Dec. 12, 2002

(65) Prior Publication Data

US 2004/0152597 A1   Aug. 5, 2004

(51) Int. Cl.
A01N 43/54 (2006.01)
A01N 57/20 (2006.01)
A07D 239/54 (2006.01)

(52) U.S. Cl. ............... 504/243; 504/242; 544/311; 544/312; 544/313; 544/314

(58) Field of Classification Search ........... 544/309, 544/310–314; 504/243, 242
See application file for complete search history.

(56) References Cited

U.S. PATENT DOCUMENTS

| | | | |
|---|---|---|---|
| 4,859,229 A * | 8/1989 | Wenger et al. ............. | 504/243 |
| 4,941,909 A * | 7/1990 | Wenger et al. ............. | 504/243 |
| 4,943,309 A | 7/1990 | Bell | |
| 5,017,211 A * | 5/1991 | Wenger et al. ............. | 504/243 |
| 6,239,074 B1 * | 5/2001 | Klintz et al. ................ | 504/168 |
| 6,451,740 B1 * | 9/2002 | Tohyama et al. ........... | 504/243 |
| 6,537,948 B1 * | 3/2003 | Tohyama et al. ........... | 504/243 |
| 6,667,413 B1 * | 12/2003 | Tohyama et al. ............ | 560/9 |

FOREIGN PATENT DOCUMENTS

| | | |
|---|---|---|
| EP | 1 106 607 A | 6/2001 |
| EP | 1 122 244 A | 8/2001 |
| WO | WO 93 11669 A | 6/1993 |
| WO | WO 0002866  * | 1/2000 |
| WO | WO 01 77084 A | 10/2001 |

* cited by examiner

Primary Examiner—Sabiha N. Qazi
(74) Attorney, Agent, or Firm—Sughrue Mion, PLLC

(57) ABSTRACT

A plant growth regulator for cotton harvest, which contains as an active ingredient, a compound of formula (I):

wherein X is CH or nitrogen; Z is halogen; A is oxygen, sulfur, or NH; $R^1$ is hydroxyl, $C_1$–$C_7$ alkoxy, $C_3$–$C_7$ alkenyloxy, $C_3$–$C_7$ alkynyloxy, $C_5$–$C_7$ cycloalkoxy, {($C_1$–$C_7$ alkoxy)carbonyl}$C_1$–$C_3$ alkoxy, ($C_1$–$C_7$ alkylamino)oxy, {di($C_1$–$C_7$ alkyl)amino}oxy, ($C_3$–$C_7$ alkylideneamino)oxy, $C_1$–$C_7$ alkylamino, di($C_1$–$C_7$ alkyl)amino, $C_3$–$C_7$ alkenylamino, $C_3$–$C_7$ alkynylamino, $C_5$–$C_7$ cycloalkylamino, {($C_1$–$C_7$ alkoxy)carbonyl}$C_1$–$C_3$ alkylamino, or ($C_1$–$C_7$ alkoxy)amino; $R^2$ is hydrogen or methyl; and $R^3$ is hydrogen, halogen, $C_1$–$C_3$ alkyl, or $C_1$–$C_3$ alkoxy.

6 Claims, No Drawings

PLANT GROWTH REGULATORS FOR COTTON HERVEST

TECHNICAL FIELD

The present invention relates to plant growth regulators which aids in cotton harvest.

BACKGROUND ART

Various plant growth regulators have been used to enable easy crop harvest. For cotton plants, plant growth regulators for harvest are applied, for example, for the purposes of (1) allowing the cotton picker to operate faster and more efficiently, (2) preventing the main source of trash, resulting in better grade cotton, (3) allowing quicker drying of morning dew so that cotton boll picking can start earlier in the day, and (4) helping stimulate cotton boll opening to enable simultaneous harvest. Commercially available plant growth regulators for cotton harvest are widely used at present. However, there has been a great demand for higher-performance plant growth regulators for cotton harvest.

DISCLOSURE OF INVENTION

The present inventor has extensively sought for novel plant growth regulators for cotton harvest. As a result, he has found that compounds of formula (I):

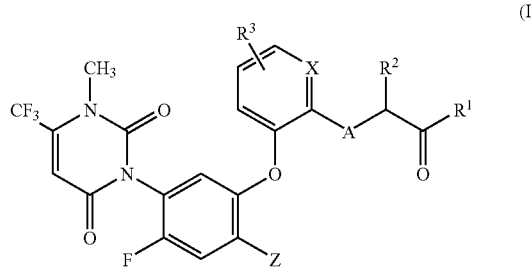

wherein X is CH or nitrogen; Z is halogen; A is oxygen, sulfur, or NH; $R^1$ is hydroxyl, $C_1$–$C_7$ alkoxy, $C_3$–$C_7$ alkenyloxy, $C_3$–$C_7$ alkynyloxy, $C_5$–$C_7$ cycloalkoxy, {($C_1$–$C_7$ alkoxy)carbonyl}$C_1$–$C_3$ alkoxy, ($C_1$–$C_7$ alkylamino)oxy, {di($C_1$–$C_7$ alkyl)amino}oxy, ($C_3$–$C_7$ alkylideneamino)oxy, $C_1$–$C_7$ alkylamino, di($C_1$–$C_7$ alkyl)-amino, $C_3$–$C_7$ alkenylamino, $C_3$–$C_7$ alkynylamino, $C_5$–$C_7$ cycloalkylamino, {($C_1$–$C_7$ alkoxy)carbonyl}$C_1$–$C_3$ alkylamino or ($C_1$–$C_7$ alkoxy)amino; $R^2$ is hydrogen or methyl; and $R^3$ is hydrogen, halogen, $C_1$–$C_3$ alkyl, or $C_1$–$C_3$ alkoxy, have excellent plant growth regulatory effects, which will be required in the cotton harvest, thereby completing the present invention.

That is, the present invention provides plant growth regulators for cotton harvest, which comprise compounds (I) as active ingredients (hereinafter referred to as the present plant growth regulator(s)).

MODE FOR CARRYING OUT THE INVENTION

The present plant growth regulators are typically used in a manner as described below.

The decisions for when to apply the present plant growth regulator are typically based on such factors as the maturity of cotton bolls and/or the percent of cotton bolls that are open or unopen. The defoliation that occurred too early may result in lower yield. Defoliation that occurred too late may increase the chance of boll rot and may be less effective as a result of lower temperatures. The present plant growth regulators are preferably applied at the time when 20% to 85% of cotton bolls have opened all over the cotton fields to be applied.

The present plant growth regulators are usually used in the form of various formulations including emulsifiable concentrates, wettable powders, flowables, and solutions, which can be prepared by mixing the compound (I) with solid carriers, liquid carriers, or other bulking agents, and if necessary, adding surfactants and other auxiliary agents thereto. In these formulations, the compounds (I) are usually contained each in an amount of 0.5% to 80% by weight, preferably 1% to 70% by weight.

The solid carrier used in the formulation may include, for example, the following materials in fine powder or granular form: clays (e.g., kaolinite, diatomaceous earth, synthetic hydrated silicon oxide, Fubasami clay, bentonite, acid clay); talc and other inorganic minerals (e.g., sericite, quartz powder, sulfur powder, activated carbon, calcium carbonate); and chemical fertilizers (e.g., ammonium sulfate, ammonium phosphate, ammonium nitrate, ammonium chloride, urea). The liquid carrier may include, for example, water; alcohols (e.g., methanol, ethanol); ketones (e.g., acetone, methyl ethyl ketone, cyclohexanone); aromatic hydrocarbons (e.g., toluene, xylene, ethyl-benzene, methylnaphthalene); non-aromatic hydrocarbons (e.g., hexane, cyclohexane, kerosine); esters (e.g., ethyl acetate, butyl acetate); nitriles (e.g., acetonitrile, isobutyronitrile); ethers (e.g., dioxane, diisopropyl ether); acid amides (e.g., dimethylformamide, dimethylacetamide); and halogenated hydrocarbons (e.g., dichloroethane, trichloroethylene).

The surfactant may include, for example, alkyl sulfate salts; alkylsulfonic acid salts; alkylarylsulfonic acid salts; alkyl aryl ethers and their polyoxyethylene derivatives; polyethylene glycol ethers; polyol esters; and sugar alcohol derivatives.

The other auxiliary agents may include, for example, adhesive agents and dispersing agents, such as casein, gelatin, polysaccharides (e.g., powdered starch, gum arabic, cellulose derivatives, alginic acid), lignin derivatives, and synthetic water-soluble polymers (e.g., polyvinyl alcohol, polyvinyl pyrrolidone, polyacrylic acid); and stabilizers such as PAP (isopropyl acid phosphate), BHT (2,6-di-tert-butyl-4-methylphenol), BHA (2-/3-tert-butyl-4-methyoxyphenol), vegetable oils, mineral oils, fatty acids, and fatty acid esters.

The present plant growth regulators thus formulated are applied to plants after diluted with water. The present plant growth regulators can be expected to have further eehanced effects by incorporation of tank mix adjuvants in water used for dilution.

The application amounts of the compounds (I) may vary with the formulations types, application times, and application places, but are usually in the range of 1 to 500 g/ha, preferably 1 to 80 g/ha.

The present plant growth regulator is usually formulated, diluted and sprayed to the above the ground parts of cotton plants (i.e. parts of the cotton plants, exposed above the soil ground) prior to cotton harvest.

In the formula (I), halogen represented by Z refers to fluorine, chlorine, bromine, or iodine;

$C_1$–$C_7$ alkoxy represented by $R^1$ may include methoxy, ethoxy, propoxy, isopropoxy, butoxy, 1-methylpropoxy, 2-methylpropoxy, pentyloxy, 1-methylbutoxy, 2-methylbutoxy, 3-methylbutoxy, 2,2-dimethylpropoxy, hexyloxy, 1-methylpentyloxy, 2-methylpentyloxy, 3-methylpentyloxy, 4-methylpentyloxy, 1,2-dimethylbutoxy, 1,3-dimethylbutoxy, 2,3-dimethylbutoxy, 3,3-dimethylbutoxy, and heptyloxy;

$C_3$–$C_7$ alkenyloxy represented by $R^1$ may include 2-propenyloxy, 3-butenyloxy, 4-pentenyloxy, 3-methyl-3-butenyloxy, and 3-methyl-2-butenyloxy;

$C_3$–$C_7$ alkynyloxy represented by $R^1$ may include 2-propynyloxy;

$C_5$–$C_7$ cycloalkoxy represented by $R^1$ may include cyclopentyloxy and cyclohexyloxy;

{($C_1$–$C_7$ alkoxy)carbonyl}$C_1$–$C_3$ alkoxy represented by $R^1$ may include methoxycarbonylmethoxy, ethoxycarbonylmethoxy, and 1-(methoxycarbonyl)-1-methylethoxy;

($C_1$–$C_7$ alkylamino)oxy represented by $R^1$ may include (methylamino)oxy and (ethylamino)oxy;

{di($C_1$–$C_7$ alkyl)amino}oxy represented by $R^1$ may include (dimethylamino)oxy and (methylethylamino)oxy;

($C_3$–$C_7$ alkylideneamino)oxy represented by $R^1$ may include (isopropylideneamino)oxy;

$C_1$–$C_7$ alkylamino represented by $R^1$ may include methylamino, ethylamino, propylamino, isopropylamino, butylamino, 1-methylpropylamino, 2-methylpropylamino, pentylamino, 1-methylbutylamino, 2-methylbutylamino, 3-methylbutylamino, 2,2-dimethylpropylamino, and hexylamino;

di($C_1$–$C_7$ alkyl)amino represented by $R^1$ may include dimethylamino and diethylamino;

$C_3$–$C_7$ alkenylamino represented by $R^1$ may include 2-propenylamino;

$C_1$–$C_7$ alkynylamino represented by $R^1$ may include 2-propynylamino;

$C_5$–$C_7$ cycloalkylamino represented by $R^1$ may include cyclopentylamino and cyclohexylamino;

{($C_1$–$C_7$ alkoxy)carbonyl}$C_1$–$C_3$ alkylamino represented by $R^1$ may include methoxycarbonylmethylamino;

($C_1$–$C_7$ alkoxy)amino represented by $R^1$ may include methoxyamino, ethoxyamino, and isopropoxyamino;

halogen represented by $R^3$ refers to fluorine, chlorine, bromine, or iodine;

$C_1$–$C_3$ alkyl represented by $R^3$ refers to methyl, ethyl, propyl, or isopropyl; and $C_1$–$C_3$ alkoxy represented by $R^3$ refers to methoxy, ethoxy, propoxy, or isopropoxy.

In the compounds of formula (I) used as the active ingredients of the present plant growth regulators, preferred are those wherein $R^1$ is methoxy or ethoxy; $R^3$ is hydrogen; and/or Z is chlorine or bromine.

Compounds (I) can be produced, for example, according to production processes A to E as described below.

Production Process A

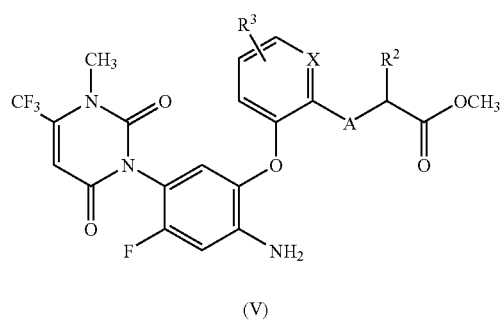

(V)

-continued

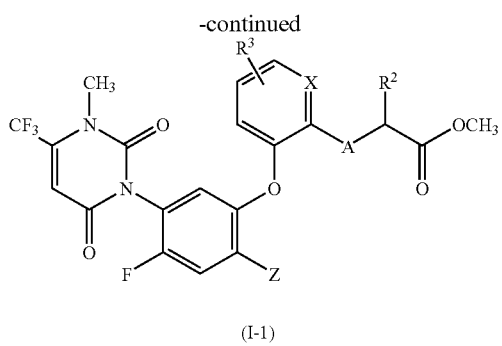

(I-1)

wherein X, Z, A, $R^2$, and $R^3$ are as defined above.

Compound (I-1) can be produced by reacting compound (V) with a diazotizing agent (first step), followed by reaction with a halide (second step).

The reaction in the first step is usually carried out at a temperature range of –20° C. to 20° C., and the reaction time is a moment to 5 hours.

The diazotizing agent used in the reaction may include nitrous acid (prepared from nitrites such as sodium nitrite, and protonic acids such as acetic acid and hydrochloric acid); nitrite esters such as isoamyl nitrite and t-butyl nitrite. The reaction is usually carried out by adding dropwise the diazotizing agent to a mixture of compound (V) and a solvent such as acetic acid, acetonitrile, or water, or preparing a diazotizing agent in the solvent.

The amounts of reagents are 1 mole of the diazotizing agent relative to 1 mole of compound (V), which is a theoretical ratio, but may suitably be changed depending upon the reaction conditions.

After the reaction in the first step, the reaction mixture is usually used as the starting material in the second step, without being subjected to separation.

The reaction in the second step is usually carried out in the range of 0° C. to 80° C., and the reaction time is a moment to 24 hours.

The halide used in the reaction may include fluorides (e.g., tetra-fluoroboric acid), chlorides (e.g., copper(I) chloride), bromides (e.g. copper(I) bromide), and iodides (e.g., potassium iodide). The reaction is usually carried out by adding dropwise the reaction mixture obtained in the first step to a mixture of a halide and a solvent such as acetic acid, acetonitrile, or water.

The amounts of reagents are 1 mole of the halide relative to 1 mole of compound (V), which is a theoretical ratio, but may suitably be changed depending upon the reaction conditions.

After completion of the reaction, for example, the reaction mixture is poured into water, which is then extracted with an organic solvent, and the organic layer is concentrated to give a desired compound.

Production Process B

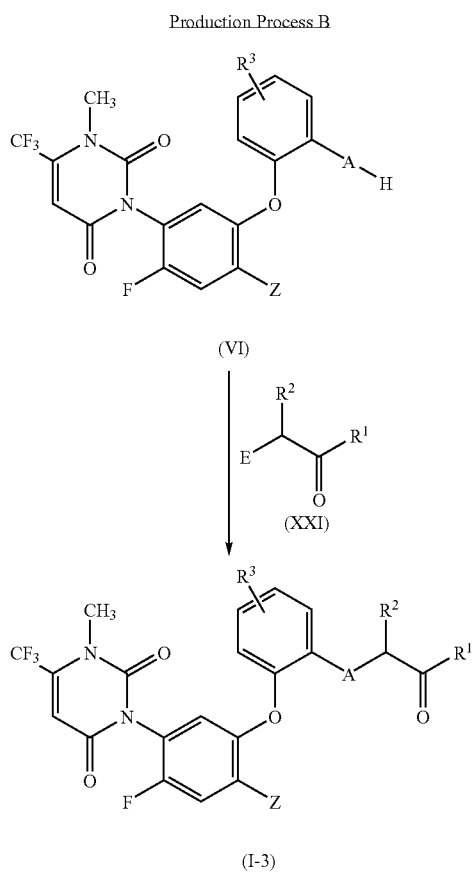

wherein E is chlorine or bromine; and Z, A, $R^1$, $R^2$, and $R^3$ are as defined above.

Compound (I-3) can be produced by reacting compound (VI) with compound (XXI) in the presence of a base in a solvent.

The reaction temperature is usually in the range of 0° C. to 150° C., and the reaction time is usually a moment to 24 hours.

The base used in the reaction may include organic bases such as pyridine, quinoline, N-methylmorpholine, 1,8-diazabicyclo[5.4.0]undec-7-ene, 1,5-azabicylco[4.3.0]non-5-ene, 1,4-diazabicyclo[2.2.2]octane, 4-dimethyl-aminopyridine, N,N-dimethylaniline, N,N-diethylaniline, triethylamine, tri-n-propylamine, and diisopropylethylamine; and inorganic bases such as sodium carbonate, potassium carbonate, sodium hydride, and potassium hydride.

The solvent used in the reaction may include aromatic hydrocarbons such as toluene and xylene; aromatic halogenated hydrocarbons such as chlorobenzene, dichlorobenzene, and benzotrifluoride; ethers such as diisopropyl ether, methyl t-butyl ether, dioxane, tetrahydrofuran, ethylene glycol dimethyl ether, and diglym; ketones such as methyl isobutyl ketone; esters such as ethyl acetate; nitro compounds such as nitromethane; nitriles such as acetonitrile; amides such as N,N-dimethylformamide and N-methyl-2-pyrollidone; sulfur compounds such as dimethylsulfoxide and sulforane; and mixtures thereof.

The amounts of reagents are 1 mole of compound (XXI) and 1 mole of the base, relative to 1 mole of compound (VI), which is a theoretical ratio, but may suitably be changed depending upon the reaction conditions.

After completion of the reaction, for example, the reaction mixture is poured into water, which is then extracted with an organic solvent, and the organic layer is concentrated to give a desired compound. The product may be purified by chromatography, recrystallization, or any other technique.

Production Process C

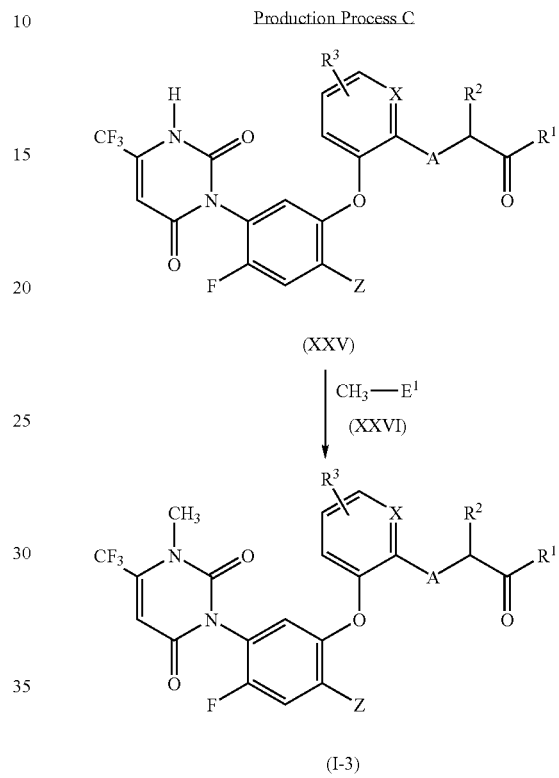

wherein $E^1$ is a leaving group such as iodine or methanesulfonyloxy, and X, Z, A, $R^1$, $R^2$, and $R^3$ are as defined above.

Compound (I-3) can be produced by reacting compound (XXV) with compound (XXVI) in the presence of a base in a solvent.

The reaction temperature is usually in the range of 0° C. to 150° C., and the reaction time is usually a moment to 24 hours.

The base used in the reaction may include organic bases such as pyridine, quinoline, N-methylmorpholine, 1,8-diazabicyclo[5.4.0]undec-7-ene, 1,5-diazabicylco[4.3.0]non-5-ene, 1,4-diazabicyclo[2.2.2]octane, 4-dimethyl-aminopyridine, N,N-dimethylaniline, N,N-diethylaniline, triethylamine, tri-n-propylamine, and diisopropylethylamine; and inorganic bases such as sodium carbonate, potassium carbonate, sodium hydride, and potassium hydride.

The solvent used in the reaction may include aromatic hydrocarbons such as toluene and xylene; aromatic halogenated hydrocarbons such as chlorobenzene, dichlorobenzene, and benzotrifluoride; ethers such as diisopropyl ether, methyl t-butyl ether, dioxane, tetrahydrofuran, ethylene glycol dimethyl ether, and diglym; ketones such as methyl isobutyl ketone; esters such as ethyl acetate; nitro compounds such as nitromethane; nitrites such as acetonitrile; amides such as N,N-dimethylformamide and N-methyl-2- pyrollidone; sulfur compounds such as dimethylsulfoxide and sulforane; and mixtures thereof.

The amounts of reagents are 1 mole of compound (XXVI) and 1 mole of the base, relative to 1 mole of compound (XXV), which is a theoretical ratio, but may suitably be changed depending upon the reaction conditions.

After completion of the reaction, for example, the reaction mixture is poured into water, which is then extracted with an organic solvent, and the organic layer is concentrated to give a desired compound. The product may be purified by chromatography, recrystallization, or any other technique.

Production Process D

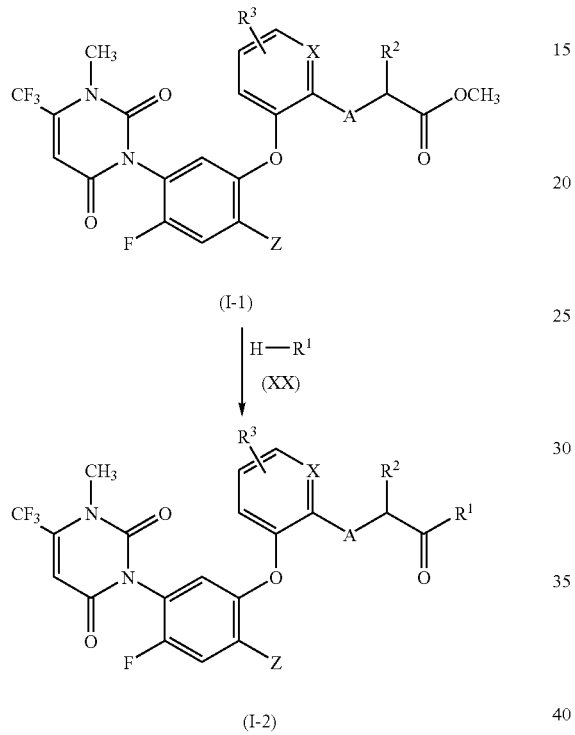

wherein X, Z, A, $R^1$, $R^2$, and $R^3$ are as defined above.

Compound (I-2) can be produced by reacting compound (I-1) with compound (XX). The reaction may be carried out in the presence of an acid or a base as a catalyst.

The reaction temperature is usually in the range of 20° C. to 150° C., and the reaction time is usually a moment to 24 hours.

The acid optionally used may include organic protonic acids such as methanesulfonic acid; and inorganic protonic acids such as sulfuric acid. The base may include organic bases such as pyridine; and inorganic bases such as sodium carbonate.

The amounts of reagents are 1 mole to an excess of compound (XX), relative to 1 mole of compound (I-1).

The reaction may involve the use of a solvent inert thereto. In the reaction, the methanol formed as a by-product may be distilled out of the reaction system, so that the rate of the reaction can be increased.

After completion of the reaction, for example, the reaction mixture is poured into water, which is then extracted with an organic solvent, and the organic layer is concentrated to give a desired compound. The product may be purified by chromatography, recrystallization, or any other technique.

Production Process E

Compound (I-2) can also be produced by reacting compound (I-4) with compound (XX) under the dehydration conditions.

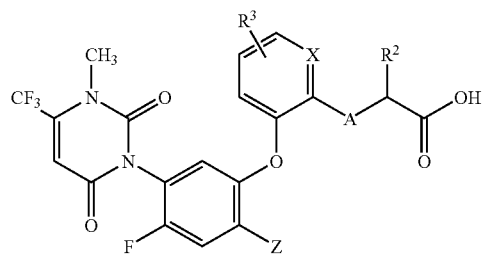

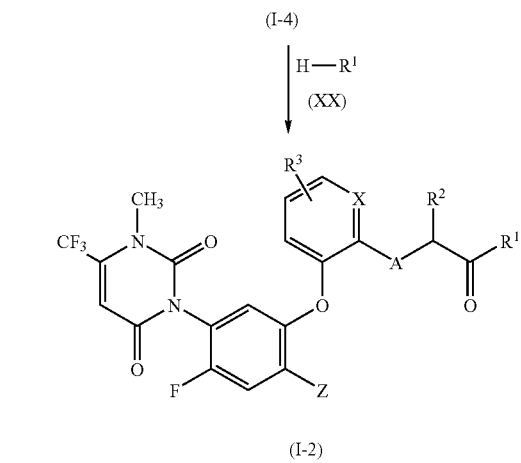

wherein X, Z, A, $R^1$, $R^2$, and $R^3$ are as defined above.

Compound (V) can be produced by the process as shown below.

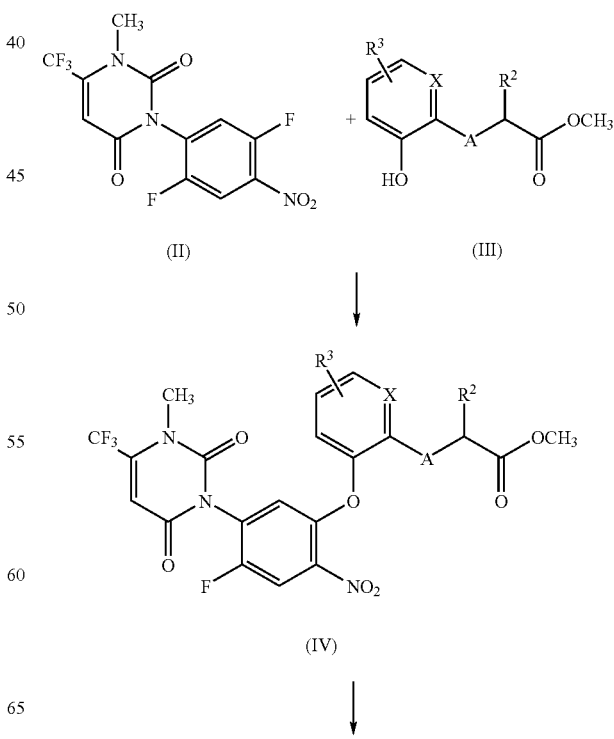

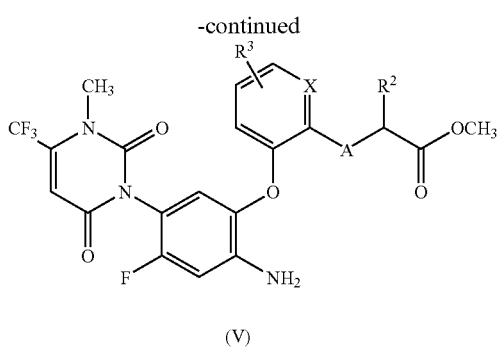

(V)

wherein X, A, R², and R³ are as defined above.

First step: The step of producing compound (IV) from compound (II) and compound (III).

Compound (IV) can be produced by reacting compound (II) with compound (III) in the presence of a base in a solvent.

The reaction temperature is usually in the range of 0° C. to 150° C., and the reaction time is usually a moment to 24 hours.

The base used in the reaction may include organic bases such as pyridine, quinoline, N-methylmorpholine, 1,8-diazabicyclo[5.4.0]undec-7-ene, 1,5-diazabicylco[4.3.0]non-5-ene, 1,4-diazabicyclo [2.2.2]octane, 4-dimethyl-aminopyridine, N,N-dimethylaniline, N,N-diethylaniline, triethylamine, tri-n-propylamine, and diisopropylethylamine; and inorganic bases such as sodium carbonate, potassium carbonate, sodium hydride, and potassium hydride.

The solvent used in the reaction may include aromatic hydrocarbons such as toluene and xylene; ethers such as dioxane; amides such as N,N-dimethylformamide and N-methyl-2-pyrollidone; sulfur compounds such as dimethylsulfoxide and sulforane; and mixtures thereof.

The amounts of reagents are 1 mole of compound (II) and 1 mole of the base, relative to 1 mole of compound (III), which is a theoretical ratio, but may suitably be changed depending upon the reaction conditions.

After completion of the reaction, for example, the reaction mixture is poured into water, which is then extracted with an organic solvent, and the organic layer is concentrated to give a desired compound. The product may be purified by chromatography, recrystallization, or any other technique.

Second step: The step of producing compound (V) from compound (IV).

Compound (V) can be produced by reacting compound (IV) with iron powder in the presence of a protonic acid.

The reaction temperature is usually in the range of 0° C. to 100° C., and the reaction time is usually a moment to 24 hours.

The protonic acid used in the reaction may include organic protonic acids such as acetic acid and propionic acid; and inorganic protonic acids such as hydrochloric acid.

The amounts of reagents are 3 moles to an excess of the iron powder and 3 moles to an excess of the acid, relative to 1 mole of compound (IV), which may suitably be changed depending upon the reaction conditions.

The reaction may involve the use of a solvent inert thereto.

After completion of the reaction, for example, the reaction mixture is filtered, and the filtrate is poured into water, which is neutralized and then extracted with an organic solvent, and the organic layer is concentrated to give a desired compound. The product may be purified by chromatography, recrystallization, or any other technique.

Compound (II) can be produced according to the process known in the art.

Compound (III) can be produced by the process as shown below.

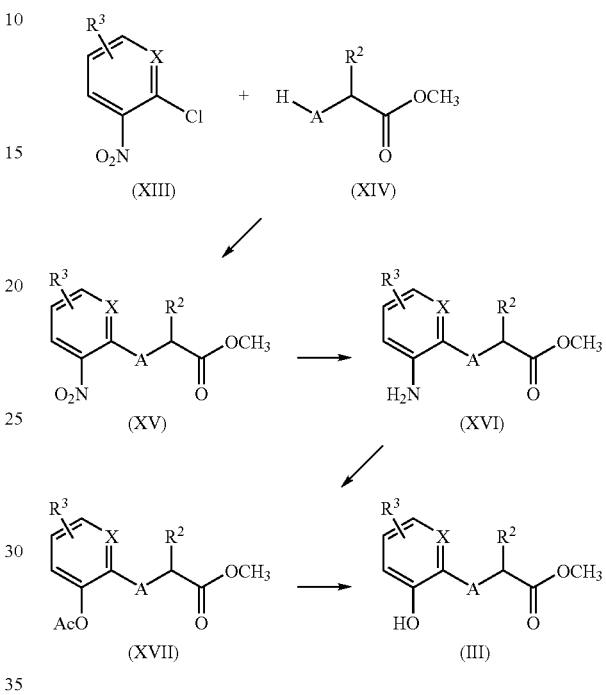

wherein X, A, R², and R³ are as defined above.

First step: The step of producing compound (XV) from compound (XIII) and compound (XIV).

Compound (XV) can be produced by reacting compound (XIII) with compound (XIV) in the presence of a base in a solvent.

Second step: The step of producing compound (XVI) from compound (XV).

Compound (XVI) can be produced by reducing compound (XV) (e.g., by a technique such as iron reduction (Fe/acetic acid) or hydrogenation (Pd—C/H₂)).

Third step: The step of producing compound (XVII) from compound (XVI).

Compound (XVII) can be produced by reacting compound (XVI) with a diazotizing agent (e.g., nitrous acid (prepared from nitrites such as sodium nitrite, and protonic acids such as acetic acid and hydrochloric acid), nitrite esters such as isoamyl nitrite and t-butyl nitrite), followed by reaction with acetic anhydride.

Fourth step: The step of producing compound (III) from compound (XVII).

Compound (III) can be produced by selective hydrolysis of compound (XVII).

Compound (XXV) can be produced according to the process described in Reference Production Example 8 or 9.

For compounds (XX), (XXI), (XXVI), and (XIV), there can be used commercially available compounds.

The present invention will hereinafter be further illustrated by some specific examples; however, the present invention is not limited only to these examples.

The following will describe production examples for the compounds of formula (I), which are designated by their compound numbers shown below in Tables 1 to 3.

PRODUCTION EXAMPLE 1

Production of Compound a-5

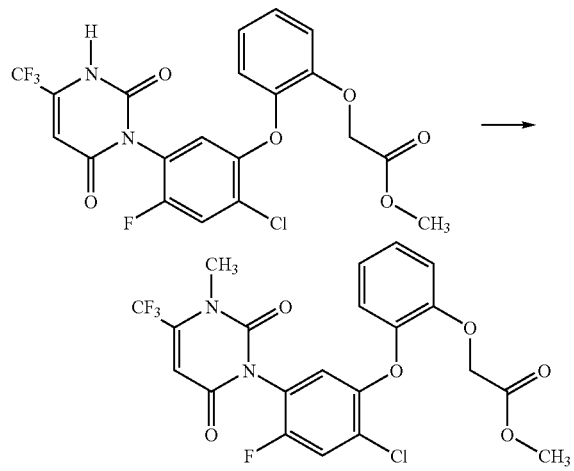

To a mixture of 0.93 g of methyl [2-{2-chloro-4-fluoro-5-[2,6-dioxo-4-(trifluoromethyl)-1,2,3,6-tetrahydropyrimidin-1-yl]phenoxy}phenoxy]acetate, 0.31 g of potassium carbonate, and 10 ml of N,N-dimethylformamide was added 0.58 g of methyl iodide, and the mixture was stirred at room temperature for 2 hours. Then 50 ml of diluted hydrochloric acid was added, and the mixture was extracted with ethyl acetate. The organic layer was washed with water, saturated aqueous sodium chloride solution, dried over anhydrous sodium sulfate, and then concentrated under reduced pressure. The residue was subjected to silica gel column chromatography to give 0.82 g of methyl [2-{2-chloro-4-fluoro-5-[3-methyl-2,6-dioxo-4-(trifluoromethyl)-1,2,3,6-tetrahydropyrimidin-1-yl]phenoxy}phenoxy]acetate (compound a-5).

$^1$H-NMR (CDCl$_3$, 250 MHz) δ(ppm): 3.49–3.50 (m, 3H), 3.73 (s, 3H), 4.66 (s, 2H), 6.28 (s, 1H), 6.76 (d, 1H, J=6.6 Hz), 6.9–7.2 (m, 4H), 7.36 (d, 1H, J=8.9 Hz).

PRODUCTION EXAMPLE 2

Production of Compound a-6

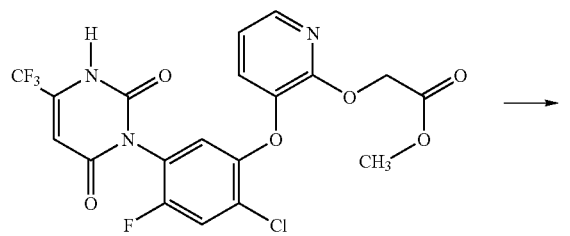

-continued

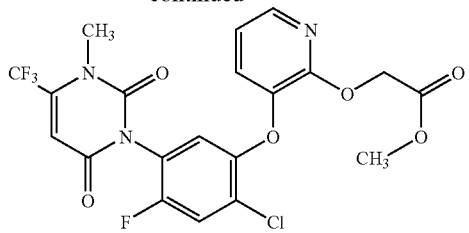

To a mixture of 0.10 g of methyl [3-{2-chloro-4-fluoro-5-[2,6-dioxo-4-(trifluoromethyl)-1,2,3,6-tetrahydropyrimidin-1-yl]phenoxy}-2-pyridyloxy]-acetate, 1 ml of acetonitrile, and 31 mg of potassium carbonate was added 32 mg of methyl iodide, and the mixture was stirred at room temperature for 1.5 hours. Then, 64 mg of methyl iodide was added, and the mixture was stirred at 50° C. for 1 hour. The mixture was filtered, and the filtrate was concentrated under reduced pressure. The residue was subjected to silica gel column chromatography to give 97 mg of methyl [3-{2-chloro-4-fluoro-5-[3-methyl-2,6-dioxo-4-(trifluoromethyl)-1,2,3,6-tetrahydropyrimidin-1-yl]phenoxy}-2-pyridyloxy]acetate (compound a-6).

PRODUCTION EXAMPLE 3

Production of Compound a-5

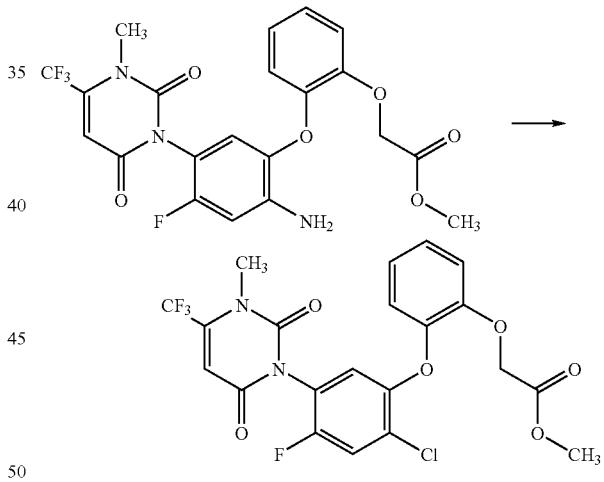

A mixture of 11.02 g of isoamyl nitrite and 45 ml of acetonitrile was added dropwise to a mixture of 15.16 g of methyl [2-{2-amino-4-fluoro-5-[3-methyl-2,6-dioxo-4-(trifluoromethyl)-1,2,3,6-tetrahydropyrimidin-1-yl]phenoxy}phenoxy]acetate, 6.21 g of copper(I) chloride, 12.65 g of copper(II) chloride, and 250 ml of acetonitrile at room temperature, and the mixture was stirred for 2 hours. The reaction mixture was poured into 2% hydrochloric acid, and the mixture was extracted with ethyl acetate. The organic layer was washed with saturated aqueous sodium chloride solution, dried over anhydrous magnesium sulfate, and then concentrated. The residue was subjected to silica gel column chromatography to give 13 g of methyl [2-{2-chloro-4-fluoro-5-[3-methyl-2,6-dioxo-4-(trifluoromethyl)-1,2,3,6-tetrahydropyrimidin-1-yl]phenoxy}phenoxy]acetate (compound a-5).

PRODUCTION EXAMPLE 4

Production of Compound a-6

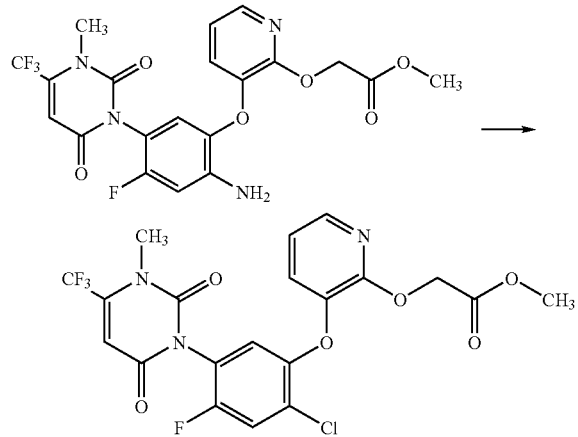

First, 88 mg of isoamyl nitrite was added dropwise to a mixture of 0.24 g of methyl [3-{2-amino-4-fluoro-5-[3-methyl-2,6-dioxo-4-(trifluoromethyl)-1,2,3,6-tetrahydropyrimidin-1-yl]phenoxy}-2-pyridyloxy]acetate, 99 mg of copper(I) chloride, 0.20 g of copper(II) chloride, and 2.5 ml of acetonitrile at room temperature, and the mixture was stirred for 1 hour. The reaction mixture was poured into 2% hydrochloric acid, and the mixture was extracted with ethyl acetate. The organic layer was washed with saturated aqueous sodium chloride solution, dried over anhydrous magnesium sulfate, and then concentrated. The residue was subjected to silica gel column chromatography to give 0.21 g of methyl [3-{2-chloro-4-fluoro-5-[3-methyl-2,6-dioxo-4-(trifluoromethyl)-1,2,3,6-tetrahydropyrimidin-1-yl]phenoxy}-2-pyridyloxy]-acetate (compound a-6).

m.p.: 52.2° C.;

$^1$H-NMR (CDCl$_3$, 300 MHz) δ(ppm): 3.50 (q, 3H, J=1.0 Hz), 3.70 (s, 3H), 4.90 (d, 1H, J=15.8 Hz), 4.97 (d, 1H, J=15.8 Hz), 6.29 (s, 1H), 6.9–7.0 (m, 2H), 7.32 (dd, 1H, J=7.7, 1.9 Hz), 7.37 (d, 1H, J=8.7 Hz), 7.92 (dd, 1H, J=4.9, 1.9 Hz).

PRODUCTION EXAMPLE 5

Production of Compound b-6

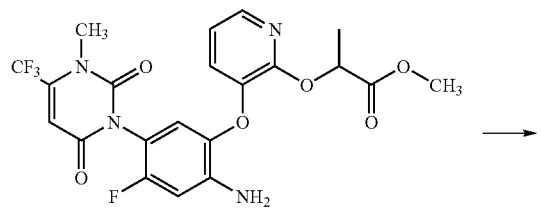

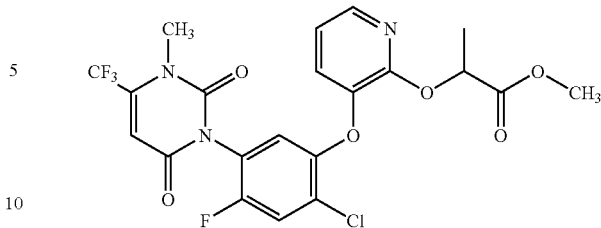

First, 18 mg of isoamyl nitrite was added dropwise to a mixture of 0.16 g of methyl 2-[3-{2-amino-4-fluoro-5-[3-methyl-2,6-dioxo-4-(trifluoromethyl)-1,2,3,6-tetrahydropyrimidin-1-yl]phenoxy}-2-pyridyloxy]propionate, 63 mg of copper(I) chloride, 129 mg of copper(II) chloride, and 1.5 ml of acetonitrile at 0° C., and the mixture was stirred for 1 hour and further stirred at room temperature for 1 hour. The reaction mixture was poured into a mixture of 1N hydrochloric acid and ice, and the mixture was extracted with ethyl acetate. The organic layer was washed with saturated aqueous sodium chloride solution, dried over anhydrous magnesium sulfate, and then concentrated. The residue was subjected to silica gel column chromatography to give 0.12 g of methyl 2-[3-{2-chloro-4-fluoro-5-[3-methyl-2,6-dioxo-4-(trifluoromethyl)-1,2,3,6-tetrahydropyrimidin-1-yl]phenoxy}-2-pyridyloxy]-propionate (compound b-6) as a mixture of diastereoisomers.

$^1$H-NMR (CDCl$_3$, 300 MHz) δ(ppm): 1.51 (d, 3/2H, J=7.0 Hz), 1.52 (d, 3/2H, J=7.0 Hz), 3.50 (s, 3H), 3.67 (s, 3H), 5.29 (q, 1/2H, J=7.0 Hz), 5.30 (q, 1/2H, J=7.0 Hz), 6.28 (s, 1/2H), 6.29 (s, 1/2H), 6.8–7.0 (m, 2H), 7.3–7.4 (m, 2H), 7.8–7.9 (m, 1H).

PRODUCTION EXAMPLE 6

Production of Compound b-10

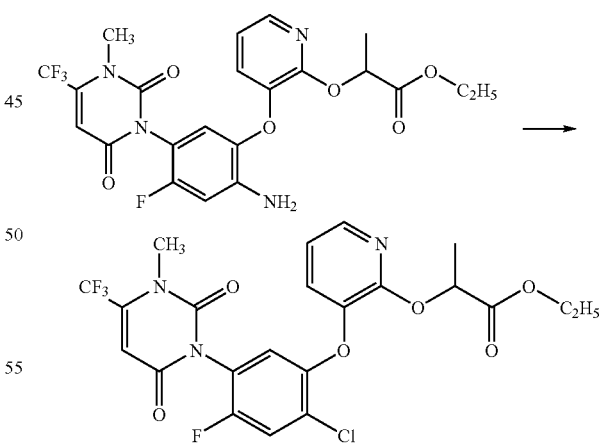

A solution of 10.99 g of isoamyl nitrite in 10 ml of acetonitrile was added to a mixture of 15.46 g of ethyl 2-[3-{2-amino-4-fluoro-5-[3-methyl-2,6-dioxo-4-(trifluoromethyl)-1,2,3,6-tetrahydropyrimidin-1-yl]phenoxy}-2-pyridyloxy]propionate, 6.19 g of copper(I) chloride, 12.61 g of copper(II) chloride, and 120 ml of acetonitrile at room temperature, and the mixture was stirred for 3 hours. The reaction mixture was poured into a mixture of ice and hydrochloric acid, and the mixture was extracted with ethyl acetate. The organic layer was washed with saturated aqueous sodium chloride solution, dried over anhydrous magnesium sulfate, and then concentrated. The residue was subjected to silica gel column chromatography to give 13.16 g of ethyl 2-[3-{2-chloro-4-fluoro-5-[3-methyl-2,6-dioxo-4-(trifluoromethyl)-1,2,3, 6-tetrahydropyrimidin-1-yl]phenoxy}-2-pyridyloxy]propionate (compound b-10).

PRODUCTION EXAMPLE 7

Production of Compound a-8

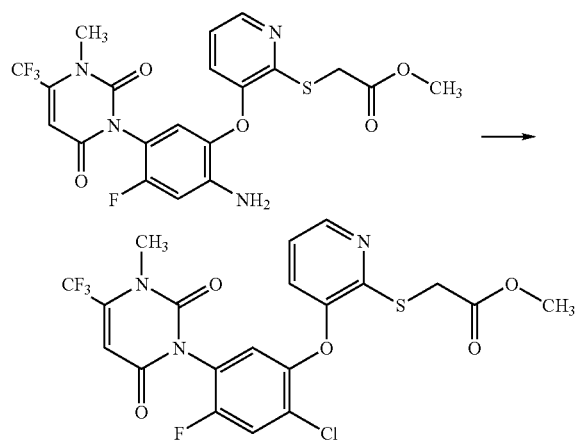

First, 92 mg of isoamyl nitrite was added dropwise to a mixture of 0.26 g of methyl [3-{2-amino-4-fluoro-5-[3-methyl-2,6-dioxo-4-(trifluoromethyl)-1,2,3,6-tetrahydropyrimidin-1-yl]phenoxy}-2-pyridylthio]acetate, 0.10 g of copper(I) chloride, 0.21 g of copper(II) chloride, and 2.5 ml of acetonitrile at room temperature, and the mixture was stirred for 1 hour. The reaction mixture was poured into 2% hydrochloric acid, and the mixture was extracted with ethyl acetate. The organic layer was washed with saturated aqueous sodium chloride solution, dried over anhydrous magnesium sulfate, and then concentrated. The residue was subjected to silica gel column chromatography to give 0.10 g of methyl [3-{2-chloro-4-fluoro-5-[3-methyl-2,6-dioxo-4-(trifluoromethyl)-1,2,3,6-tetrahydropyrimidin-1-yl]phenoxy}-2-pyridylthio]acetate (compound a-8).

$^1$H-NMR (CDCl$_3$, 300 MHz) δ(ppm): 3.54 (s, 3H), 3.75 (s, 3H), 4.01 (s, 2H), 6.33 (s, 1H), 6.9–7.0 (m, 3H), 7.42 (d, 1H, J=9.0 Hz), 8.20 (dd, 1H, J=4.1, 2.2 Hz).

PRODUCTION EXAMPLE 8

Production of Compound a-108

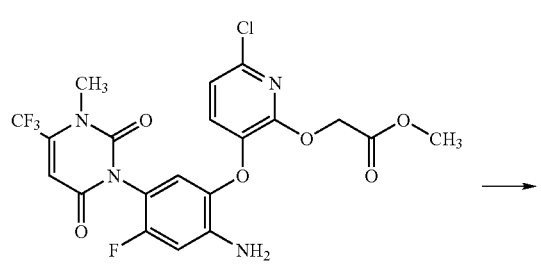

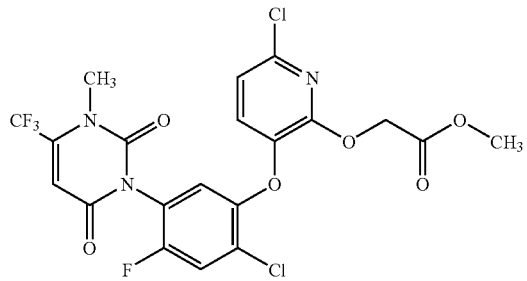

First, isoamyl nitrite is added dropwise to a mixture of methyl [3-{2-amino-4-fluoro-5-[3-methyl-2,6-dioxo-4-(trifluoromethyl)-1,2,3,6-tetrahydropyrimidin-1-yl]phenoxy}-6-chloro-2-pyridyloxy]acetate, copper(I) chloride, copper (II) chloride, and acetonitrile at room temperature, and the mixture is stirred for 1 hour. The reaction mixture is poured into 2% hydrochloric acid, and the mixture is extracted with ethyl acetate. The organic layer is washed with saturated aqueous sodium chloride solution, dried over anhydrous magnesium sulfate, and then concentrated. The residue is subjected to silica gel column chromatography to give methyl [3-{2-chloro-4-fluoro-5-[3-methyl-2,6-dioxo-4-(trifluoromethyl)-1,2,3,6-tetrahydropyrimidin-1-yl]phenoxy}-6-chloro-2-pyridyloxy]acetate (compound a-108).

PRODUCTION EXAMPLE 9

Production of Compound a-118

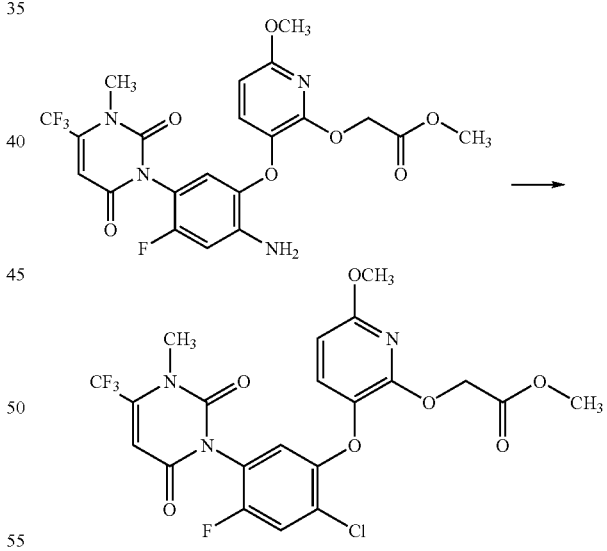

First, isoamyl nitrite is added dropwise to a mixture of methyl [3-{2-amino-4-fluoro-5-[3-methyl-2,6-dioxo-4-(trifluoromethyl)-1,2,3,6-tetrahydropyrimidin-1-yl]phenoxy}-6-methoxy-2-pyridyloxy]acetate, copper(I) chloride, copper (II) chloride, and acetonitrile at room temperature, and the mixture is stirred for 1 hour. The reaction mixture is poured into 2% hydrochloric acid, and the mixture is extracted with ethyl acetate. The organic layer is washed with saturated aqueous sodium chloride solution, dried over anhydrous magnesium sulfate, and then concentrated. The residue is subjected to silica gel column chromatography to give methyl [3-{2-chloro-4-fluoro-5-[3-methyl-2,6-dioxo-4-(trifluoromethyl)-1,2,3,6-tetrahydropyrimidin-1-yl]phenoxy}-6-methoxy-2-pyridyloxy]acetate (compound a-118).

PRODUCTION EXAMPLE 10 production of Compound b-5

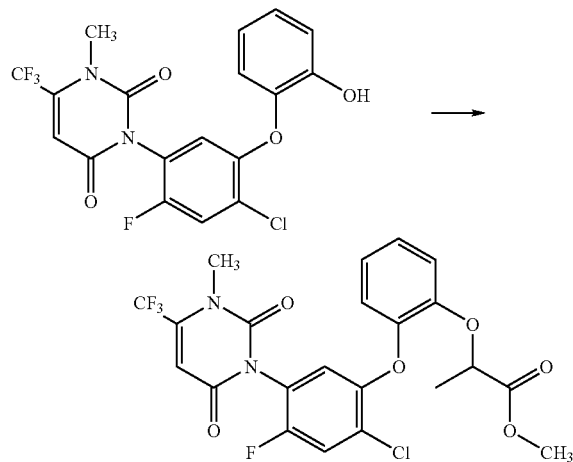

First, 0.23 g of 2-{2-chloro-4-fluoro-5-[3-methyl-2,6-dioxo-4-(trifluoromethyl)-1,2,3,6-tetrahydropyrimidin-1-yl]phenoxy}phenol was dissolved in 6 ml of N,N-dimethylformamide, to which 0.22 g of potassium carbonate was added and 0.13 g of methyl 2-bromopropionate was added under stirring at room temperature, and the mixture was stirred at 80° C. for 3 hours. The reaction mixture was cooled to room temperature and then poured into ice water, and the mixture was extracted with ethyl acetate. The organic layer was washed with saturated aqueous sodium chloride solution, dried over anhydrous magnesium sulfate, and then concentrated. The residue was subjected to silica gel column chromatography to give 0.23 g of methyl 2-[2-{2-chloro-4-fluoro-5-[3-methyl-2,6-dioxo-4-(trifluoromethyl)-1,2,3,6-tetrahydropyrimidin-1-yl]phenoxy}phenoxy]propionate (compound b-5).

$^1$H-NMR (CDCl$_3$, 250 MHz) δ(ppm): 1.47 (d, 3H, J=6.8 Hz), 3.50 (q, 3H, J=0.7 Hz), 3.6–3.8 (m, 3H), 4.6–4.8 (m, 1H), 6.28 (s, 1H), 6.7–6.8 (m, 1H), 6.8–6.9 (m, 1H), 6.9–7.1 (m, 1H), 7.1–7.2 (m, 2H), 7.3–7.4 (m, 1H).

PRODUCTION EXAMPLE 11

Production of Compound a-121

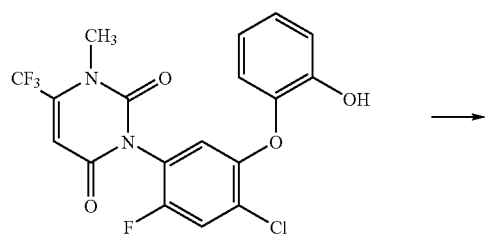

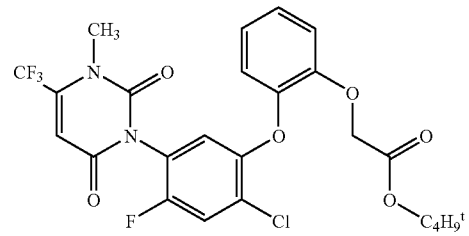

First, 0.20 g of 2-{2-chloro-4-fluoro-5-[3-methyl-2,6-dioxo-4-(trifluoromethyl)-1,2,3,6-tetrahydropyrimidin-1-yl]phenoxy}phenol was dissolved in 2 ml of N,N-dimethylformamide, to which 0.083 g of potassium carbonate was added, and the mixture was stirred at room temperature for 50 minutes. Then, 0.077 g of t-butyl chloroacetate was added, and the mixture was stirred at 40° C. to 60° C. for 2 hours. After left for cooling, ice water was poured into the reaction mixture, and after addition of ethyl acetate and saturated aqueous sodium chloride solution, the mixture was subjected to phase separation. The organic layer was washed with saturated aqueous sodium chloride solution, dried over magnesium sulfate, and then concentrated. The residue was subjected to silica gel column chromatography (eluent: n-hexane/ethyl acetate=6/1) to give 10.39 g of t-butyl [2-{2-chloro-4-fluoro-5-[3-methyl-2,6-dioxo-4-(trifluoromethyl)-1,2,3,6-tetrahydropyrimidin-1-yl]phenoxy}phenoxy]acetate (compound a-121).

$^1$H-NMR (CDCl$_3$, 250 MHz) δ(ppm): 1.44 (s, 9H), 3.49 (d, 3H, J=1.1 Hz), 4.53 (s, 2H), 6.27 (s, 1H), 6.80 (d, 1H, J=6.6 Hz), 6.8–7.2 (m, 4H), 7.35 (d, 1H, J=8.9 Hz);

m.p.: 55.6° C.

The physical properties of compounds produced by the same process as described in Production Examples 10 and 11 are shown below.

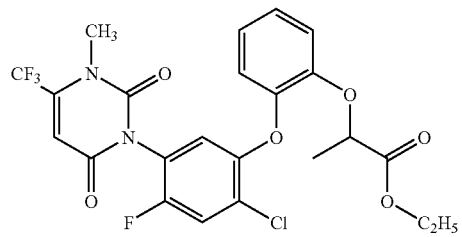

Ethyl 2-[2-{2-chloro-4-fluoro-5-[3-methyl-2,6-dioxo-4-(trifluoromethyl)-1,2,3,6-tetrahydropyrimidin-1-yl]phenoxy}phenoxy]propionate (compound b-9)

$^1$H-NMR (CDCl$_3$, 250 MHz) δ(ppm): 1.23 (t, 3H, J=7.1 Hz), 1.47 (d, 3H, J=6.8 Hz), 3.50 (s, 3H), 4.1–4.3 (m, 2H), 4.6–4.8 (m, 1H), 6.3–6.4 (m, 1H), 6.7–7.0 (m, 3H), 7.0–7.2 (m, 2H), 7.3–7.4 (m, 1H).

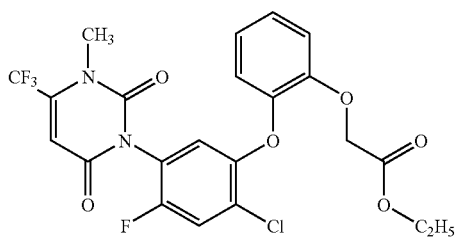

Ethyl [2-{2-chloro-4-fluoro-5-[3-methyl-2,6-dioxo-4-(trifluoromethyl)-1,2,3,6-tetrahydropyrimidin-1-yl]phenoxy}phenoxy]acetate (compound a-9)

$^1$H-NMR (CDCl$_3$, 300 MHz) δ(ppm): 1.26 (t, 3H, J=7.1 Hz), 3.50 (s, 3H), 4.19 (q, 2H, J=7.2 Hz), 4.64 (s, 2H), 6.28 (s, 1H), 6.7–6.8 (m, 1H), 6.9–7.2 (m, 4H), 7.36 (d, 1H, J=8.8 Hz).

PRODUCTION EXAMPLE 12

Production of Compound a-28

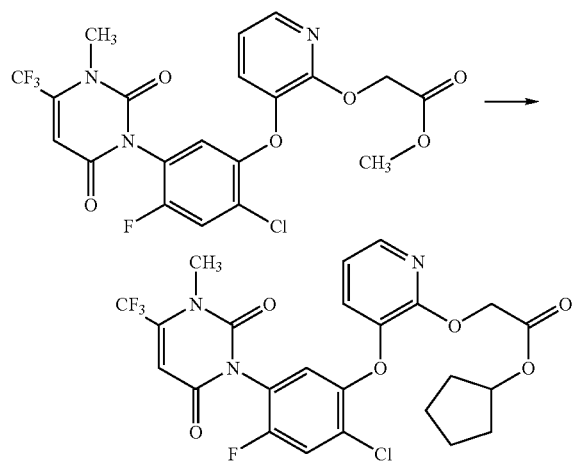

A mixture of 0.30 g of methyl [3-{2-chloro-4-fluoro-5-[3-methyl-2,6-dioxo-4-(trifluoromethyl)-1,2,3,6-tetrahydropyrimidin-1-yl]phenoxy}-2-pyridyloxy]acetate (compound a-6), 0.06 g of sodium carbonate, and 3.0 ml of cyclopentanol was stirred at 100° C. for 1.5 hours and then at 120° C. for 2 hours. The reaction mixture was cooled to room temperature and then poured into water, and the mixture was extracted with ethyl acetate. The organic layer was washed with saturated aqueous sodium chloride solution, dried over anhydrous magnesium sulfate, and then concentrated. The residue was subjected to silica gel column chromatography to give 0.15 g of cyclopentyl [3-{2-chloro-4-fluoro-5-[3-methyl-2,6-dioxo-4-(trifluoromethyl)-1,2,3,6-tetrahydropyrimidin-1-yl]phenoxy}-2-pyridyloxy]acetate (compound a-28).

PRODUCTION EXAMPLE 13

Production of Compound a-10

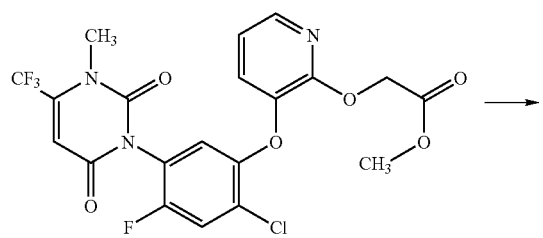

-continued

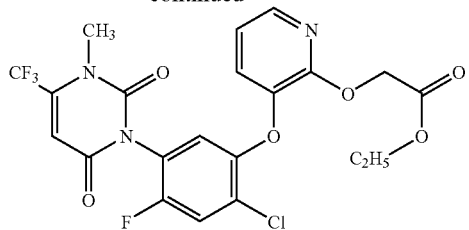

A mixture of 0.60 g of methyl [3-{2-chloro-4-fluoro-5-[3-methyl-2,6-dioxo-4-(trifluoromethyl)-1,2,3,6-tetrahydropyrimidin-1-yl]phenoxy}-2-pyridyloxy]acetate (compound a-6), 0.13 g of sodium carbonate, and 7.0 ml of ethanol was heated at reflux for 2 hours. After cooling to room temperature, the solvent was distilled out under reduced pressure, and the residue was subjected to silica gel chromatography to give 0.55 g of ethyl [3-{2-chloro-4-fluoro-5-[3-methyl-2,6-dioxo-4-(trifluoromethyl)-1,2,3,6-tetrahydropyrimidin-1-yl]phenoxy}-2-pyridyloxy]acetate (compound a-10).

$^1$H-NMR (CDCl$_3$, 250 MHz) δ(ppm): 1.25 (t, 3H, J=7.1 Hz), 3.50 (q, 3H, J=1.2 Hz), 4.16 (q, 2H, J=7.1 Hz), 4.88 (d, 1H, J=15.9 Hz), 4.96 (d, 1H, J=15.9 Hz), 6.29 (s, 1H), 6.9–7.0 (m, 2H), 7.3–7.4 (m, 2H), 7.9–8.0 (m, 1H).

PRODUCTION EXAMPLE 14

Production of Compound a-14

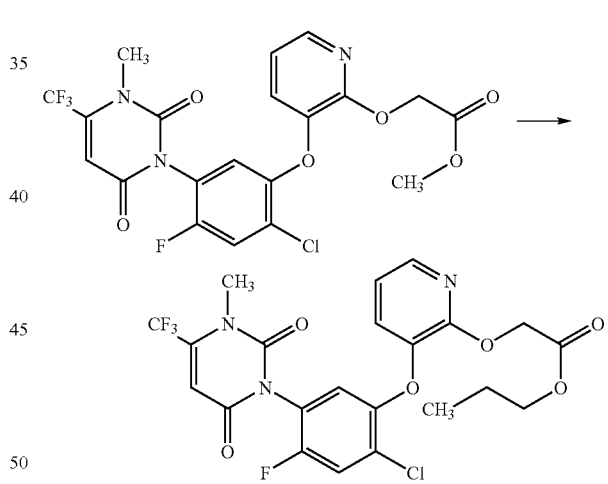

A mixture of 0.60 g of methyl [3-{2-chloro-4-fluoro-5-[3-methyl-2,6-dioxo-4-(trifluoromethyl)-1,2,3,6-tetrahydropyrimidin-1-yl]phenoxy}-2-pyridyloxy]acetate (compound a-6), 0.13 g of sodium carbonate, and 7.0 ml of n-propanol was stirred under reflux for 2 hours. After cooling to room temperature, the solvent was distilled out under reduced pressure, and the residue was subjected to silica gel column chromatography to give propyl [3-{2-chloro-4-fluoro-5-[3-methyl-2,6-dioxo-4-(trifluoromethyl)-1,2,3,6-tetrahydropyrimidin-1-yl]phenoxy}-2-pyridyloxy]acetate (compound a-14).

$^1$H-NMR (CDCl$_3$, 300 MHz) δ(ppm): 0.89 (t, 3H, J=7.3 Hz), 1.63 (qt, 2H, J=7.3, 6.5 Hz), 3.50 (q, 3H, J=0.8 Hz), 4.06 (t, 2H, J=6.5 Hz), 4.89 (d, 1H, J=16.0 Hz), 4.97 (d, 1H, J=16.0 Hz), 6.28 (s, 1H), 6.91 (dd, 1H, J=7.8, 5.0 Hz), 6.93

(d, 1H, J=6.5 Hz), 7.31 (dd, 1H, J=7.8, 1.6 Hz), 7.36 (d, 1H, J=8.9 Hz), 7.91 (dd, 1H, J=5.0, 1.6 Hz).

PRODUCTION EXAMPLE 15

Production of Compound a-20

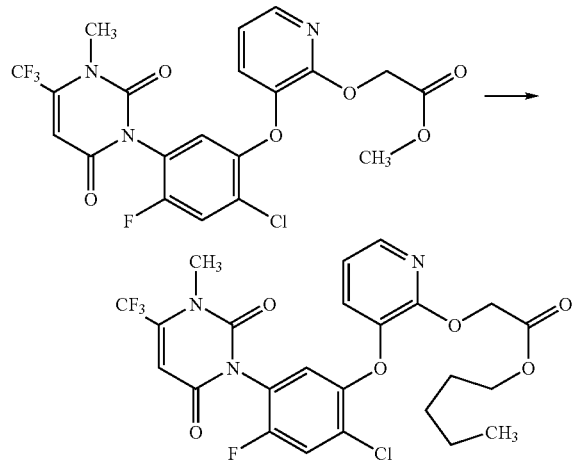

A mixture of 0.30 g of methyl [3-{2-chloro-4-fluoro-5-[3-methyl-2,6-dioxo-4-(trifluoromethyl)-1,2,3,6-tetrahydropyrimidin-1-yl]phenoxy}-2-pyridyloxy]acetate (compound a-6), 0.06 g of sodium carbonate, and 3.0 ml of n-pentanol was stirred at 100° C. for 1.5 hours. After cooling to room temperature, the reaction mixture was poured into water, and the mixture was extracted with ethyl acetate. The organic layer was washed with saturated aqueous sodium chloride solution, dried over anhydrous magnesium sulfate, and then concentrated. The residue was subjected to silica gel column chromatography to give 0.07 g of pentyl [3-{2-chloro-4-fluoro-5-[3-methyl-2,6-dioxo-4-(trifluoromethyl)-1,2,3,6-tetrahydropyrimidin-1-yl]phenoxy}-2-pyridyloxy]-acetate (compound a-20).

$^1$H-NMR (CDCl$_3$, 300 MHz) δ(ppm): 0.88 (t, 3H, J=6.6 Hz), 1.2–1.4 (m, 4H), 1.5–1.7 (m, 2H), 3.50 (q, 3H, J=1.0 Hz), 4.0–4.2 (m, 2H), 4.8–5.1 (m, 2H), 6.29 (s, 1H), 6.9–7.0 (m, 2H), 7.28 (dd, 1H, J=7.9, 1.4 Hz), 7.37 (d, 1H, J=9.0 Hz), 7.91 (dd, 1H, J=4.9, 1.4 Hz).

PRODUCTION EXAMPLE 16

Production of Compound b-19

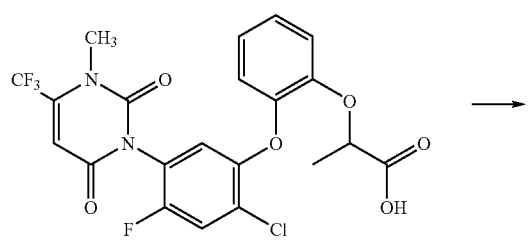

-continued

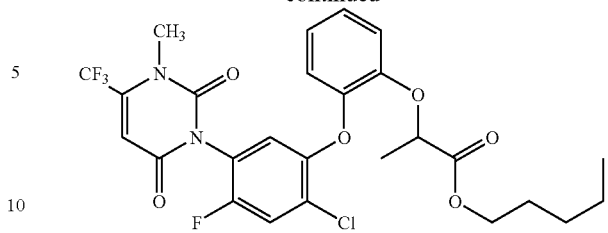

First, 2-[2-{2-chloro-4-fluoro-5-[3-methyl-2,6-dioxo-4-(trifluoromethyl)-1,2,3,6-tetrahydropyrimidin-1-yl]phenoxy}phenoxy]propionic acid (compound b-1) is dissolved in tetrahydrofuran, to which thionyl chloride is added under stirring, and the mixture is heated and stirred under reflux. After left for cooling and the subsequent concentration, the residue is dissolved in tetrahydrofuran (hereinafter referred to as solution A). Tetrahydrofuran is added to 1-pentyl alcohol, to which solution A id added and pyridine is then added. After stirring at room temperature, 2% aqueous hydrochloric acid is added to the reaction mixture, and the mixture is extracted with ethyl acetate. The organic layer is washed with saturated aqueous sodium chloride solution, dried over magnesium sulfate, and then concentrated. The residue is subjected to silica gel column chromatography (eluent: hexane/ethyl acetate=5/1) to give pentyl 2-[2-{2-chloro-4-fluoro-5-[3-methyl-2,6-dioxo-4-(trifluoromethyl)-1,2,3,6-tetrahydropyrimidin-1-yl]phenoxy}phenoxy]propionate (compound b-19).

PRODUCTION EXAMPLE 17

Production of Compound a-21

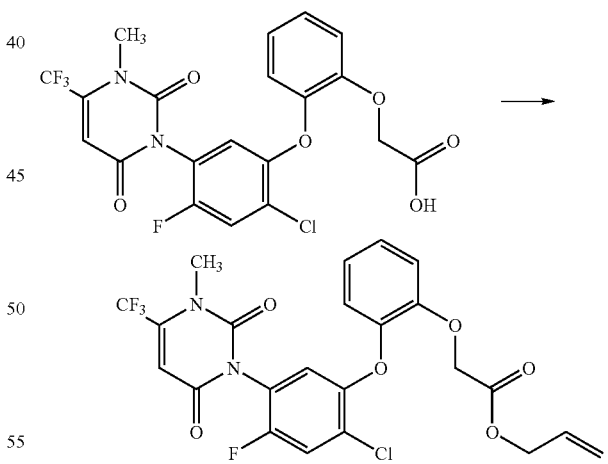

First, 1.0 g of [2-{2-chloro-4-fluoro-5-[3-methyl-2,6-dioxo-4-(trifluoromethyl)-1,2,3,6-tetrahydropyrimidin-1-yl]phenoxy}phenoxy]acetic acid (compound a-1) was dissolved in tetrahydrofuran, to which 0.7 ml of thionyl chloride was added under stirring, and the mixture was heated and stirred under reflux for 2 hours. After left for cooling and the subsequent concentration, the residue was dissolved in 3 ml of tetrahydrofuran (hereinafter referred to as solution B). Then, 0.7 ml of tetrahydrofuran was added to 0.05 g of allyl alcohol, to which a third part of solution B was added and 0.17 ml of pyridine was then added. After stirring at room temperature for 2 hours, 2% aqueous hydrochloric acid was poured into the reaction mixture, and the mixture was extracted with ethyl acetate. The organic layer was washed with saturated aqueous sodium chloride solution, dried over magnesium sulfate, and then concentrated. The residue was subjected to silica gel column chromatography (eluent: hexane/ethyl acetate=5/1) to give 0.08 g of allyl [2-{2-chloro-4-fluoro-5-[3-methyl-2,6-dioxo-4-(trifluoromethyl)-1,2,3,6-tetrahydropyrimidin-1-yl]phenoxy}phenoxy]acetate (compound a-21).

$^1$H-NMR (CDCl$_3$, 300 MHz) δ(ppm): 3.50 (d, 3H, J=1.2 Hz), 4.62–4.64 (m, 2H), 4.68 (s, 2H), 5.22–5.32 (m, 2H), 5.8–6.0 (m, 1H), 6.28 (s, 1H), 6.76 (d, 1H, J=6.5 Hz), 6.91–7.14 (m, 4H), 7.35 (d, 1H, J=8.6 Hz).

PRODUCTION EXAMPLE 18

Production of Compound a-123

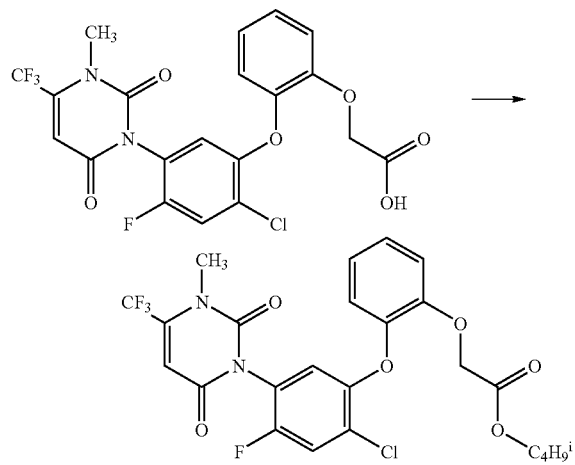

First, 1.5 g of [2-{2-chloro-4-fluoro-5-[3-methyl-2,6-dioxo-4-(trifluoromethyl)-1,2,3,6-tetrahydropyrimidin-1-yl]phenoxy}phenoxy]acetic acid (compound a-1) was dissolved in 6 ml, to which 1 ml of thionyl chloride was added under stirring, and the mixture was heated and stirred under reflux for 2 hours and 10 minutes. After left for cooling and the subsequent concentration, the residue was dissolved in 3 ml of tetrahydrofuran (hereinafter referred to as solution C). Then, 1 ml of tetrahydrofuran was added to 0.273 g of isobutyl alcohol, to which a third part of solution C was added and 0.25 ml of pyridine was then added. After stirring at room temperature for 2 hours, 2% aqueous hydrochloric acid was poured into the reaction mixture, to which ethyl acetate was added, and the mixture was subjected to phase separation. The organic layer was washed with saturated aqueous sodium chloride solution, dried over magnesium sulfate, and then concentrated. The residue was subjected to silica gel column chromatography (eluent: hexane/ethyl acetate=6/1) to give 0.34 g of isobutyl [2-{2-chloro-4-fluoro-5-[3-methyl-2,6-dioxo-4-(trifluoromethyl)-1,2,3,6-tetrahydropyrimidin-1-yl]phenoxy}phenoxy]acetate (compound a-123).

$^1$H-NMR (CDCl$_3$, 250 MHz) δ(ppm): 0.89 (d, 6H, J=6.7 Hz), 1.8–2.0 (m, 1H), 3.50 (d, 3H, J=1.2 Hz), 3.92 (d, 2H, J=6.7 Hz), 4.67 (s, 2H), 6.28 (s, 1H), 6.77 (d, 1H, J=6.6 Hz), 6.85–7.15 (m, 4H), 7.36 (d, 1H, J=8.9 Hz).

PRODUCTION EXAMPLE 19

Production of Compound a-104

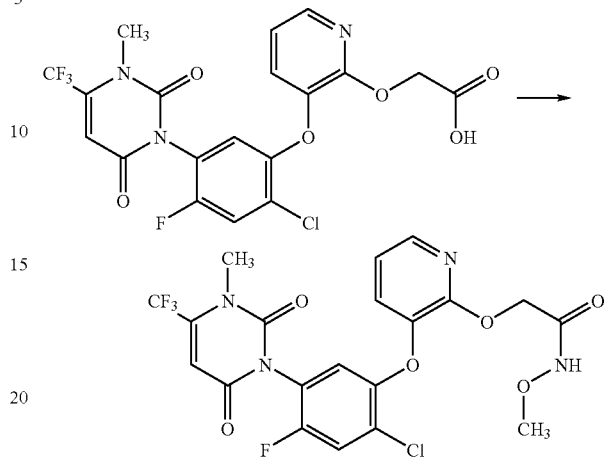

First, 0.13 g of 1-[3-(dimethylamino)propyl]-3-ethylcarbodiimide hydrochloride was added to a mixture of 0.30 g of [3-{2-chloro-4-fluoro-5-[3-methyl-2,6-dioxo-4-(trifluoromethyl)-1,2,3,6-tetrahydropyrimidin-1-yl]phenoxy}-2-pyridyloxy]acetic acid (compound a-2), 56 mg of o-methylhydroxylamine, 68 mg of triethylamine, and 2 ml of N,N-dimethylformamide at room temperature, and the mixture was stirred for 2 hours. The mixture was poured into water, and the mixture was extracted with ethyl acetate. The organic layer was dried over anhydrous magnesium sulfate and then concentrated. The residue was subjected to silica gel column chromatography to give 90 mg of N-methoxy-[3-{2-chloro-4-fluoro-5-[3-methyl-2,6-dioxo-4-(trifluoromethyl)-1,2,3,6-tetrahydropyrimidin-1-yl]phenoxy}-2-pyridyloxy]acetamide (compound a-104).

$^1$H-NMR (CDCl$_3$, 300 MHz) δ(ppm): 3.52 (s, 3H), 3.74 (s, 3H), 4.87 (s, 2H), 6.32 (s, 1H), 6.71 (d, 1H, J=6.0 Hz), 6.99 (dd, 1H, J=7.6, 5.0 Hz), 7.38 (dd, 1H, J=7.6, 1.7 Hz), 7.44 (d, 1H, J=8.7 Hz), 8.00 (dd, 1H, J=5.0, 1.7 Hz), 8.7–9.0 (bs, 1H).

PRODUCTION EXAMPLE 20

Production of Compound a-32

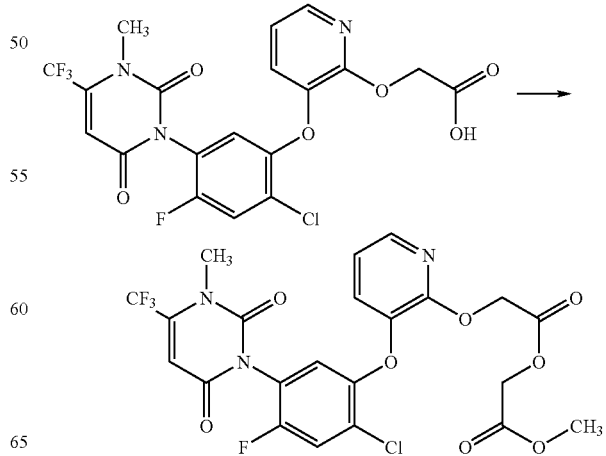

First, 0.13 g of 1-[3-(dimethylamino)propyl]-3-ethylcarbodiimide hydrochloride was added to a mixture of 0.30 g of [3-{2-chloro-4-fluoro-5-[3-methyl-2,6-dioxo-4-(trifluoromethyl)-1,2,3,6-tetrahydropyrimidin-1-yl]phenoxy}-2-pyridyloxy]acetic acid (compound a-2), 60 mg of methyl glycolate, and 2 ml of N,N-dimethylformamide at room temperature, and the mixture was stirred for 1.5 hours. The mixture was poured into water, and the mixture was extracted with ethyl acetate. The organic layer was dried over anhydrous magnesium sulfate and then concentrated. The residue was subjected to silica gel column chromatography to give 0.18 g of methyl [3-{2-chloro-4-fluoro-5-[3-methyl-2,6-dioxo-4-(trifluoromethyl)-1,2,3,6-tetrahydropyrimidin-1-yl]phenoxy}-2-pyridyloxy]acetoxyacetate (compound a-32).

$^1$H-NMR (CDCl$_3$, 300 MHz) δ(ppm): 3.50 (s, 3H), 3.74 (s, 3H), 4.65 (s, 2H), 5.01 (d, 1H, J=16.2 Hz), 5.09 (d, 1H, J=16.2 Hz), 6.28 (s, 1H), 6.88 (d, 1H, J=6.7 Hz), 6.93 (dd, 1H, J=7.8, 4.9 Hz), 7.32 (dd, 1H, J=7.8, 1.4 Hz), 7.37 (d, 1H, J=9.0 Hz), 7.93 (dd, 1H, J=4.9, 1.4 Hz).

PRODUCTION EXAMPLE 21

Production of Compound a-98

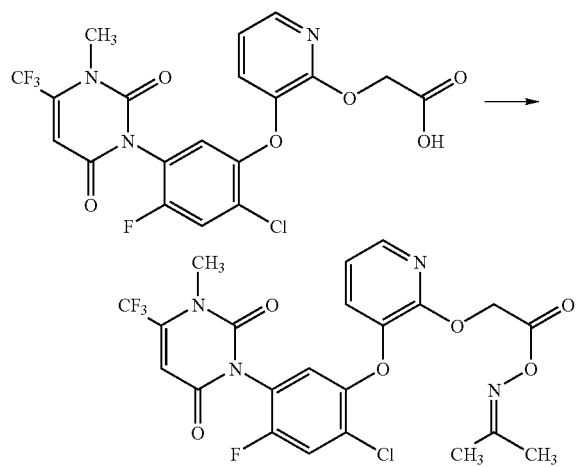

First, 0.13 g of 1-[3-(dimethylamino)propyl]-3-ethylcarbodiimide hydrochloride was added to a mixture of 0.30 g of [3-{2-chloro-4-fluoro-5-[3-methyl-2,6-dioxo-4-(trifluoromethyl)-1,2,3,6-tetrahydropyrimidin-1-yl]phenoxy}-2-pyridyloxy]acetic acid (compound a-2), 49 mg of acetone oxime, and 2 ml of N,N-dimethylformamide at room temperature, and the mixture was stirred for 2 hours. The mixture was poured into water, and the mixture was extracted with ethyl acetate. The organic layer was dried over anhydrous magnesium sulfate and then concentrated. The residue was subjected to silica gel column chromatography to give 0.16 g of acetone O-[3-{2-chloro-4-fluoro-5-[3-methyl-2,6-dioxo-4-(trifluoromethyl)-1,2,3,6-tetrahydropyrimidin-1-yl]phenoxy}-2-pyridyloxy]acetyloxime (compound a-98).

$^1$H-NMR (CDCl$_3$, 300 MHz) δ(ppm): 1.94 (s, 3H), 2.01 (s, 3H), 3.49 (s, 3H), 5.0–5.2 (m, 2H), 6.27 (s, 1H), 6.92 (dd, 1H, J=7.8, 4.9 Hz), 6.98 (d, 1H, J=6.5 Hz), 7.3–7.4 (m, 2H), 7.92 (d, 1H, J=4.9 Hz).

The following will describe production examples for intermediates in the production of compounds (I).

REFERENCE PRODUCTION EXAMPLE 1

Step 1:

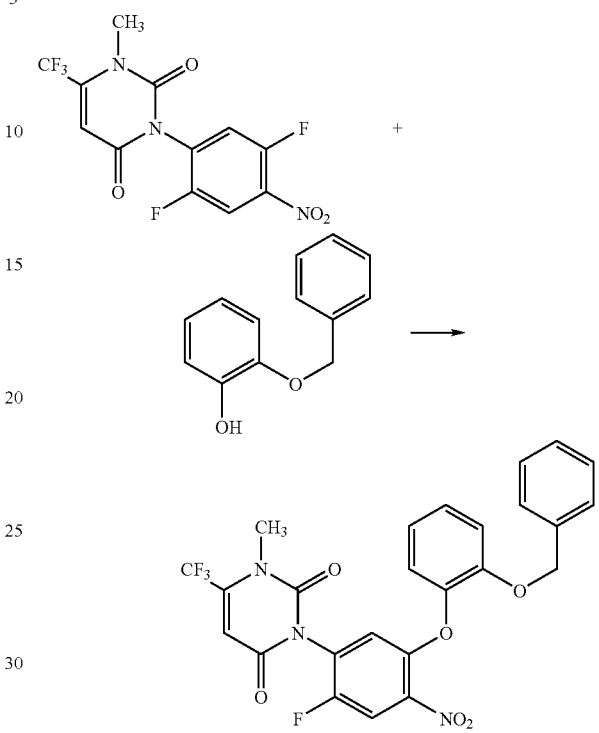

A mixture of 4.05 g of 2-benzyloxyphenol and 9.5 ml of N,N-dimethylformamide was added dropwise to a mixture of 0.80 g of sodium hydride and 20 ml of N,N-dimethylformamide under ice cooling, and the mixture was stirred for 30 minutes. A mixture of 7.1 g of 2,5-difluoro-4-[3-methyl-2,6-dioxo-4-(trifluoromethyl)-1,2,3,6-tetrahydropyrimidin-1-yl]nitrobenzene and 17 ml of N,N-dimethylformamide was added dropwise at the same temperature, and the mixture was stirred for 1 hour. The reaction mixture was poured into ice water, and the mixture was extracted with ethyl acetate. The organic layer was washed once with 1N hydrochloric acid and once with saturated aqueous sodium chloride solution, dried over anhydrous magnesium sulfate, and then concentrated. The residue was subjected to silica gel column chromatography to give 8.6 g of 2-(2-benzyloxyphenoxy)-5-fluoro-4-[3-methyl-2,6-dioxo-4-(trifluoromethyl)-1,2,3,6-tetrahydropyrimidin-1-yl]-nitrobenzene.

$^1$H-NMR (CDCl$_3$, 250 MHz) δ(ppm): 3.52 (q, 3H, J=1.1 Hz), 5.01 (s, 2H), 6.31 (s, 1H), 6.81 (d, 1H, J=6.0 Hz), 6.9–7.1 (m, 2H), 7.1–7.4 (m, 7H), 7.78 (d, 1H, J=8.7 Hz).

Step 2:

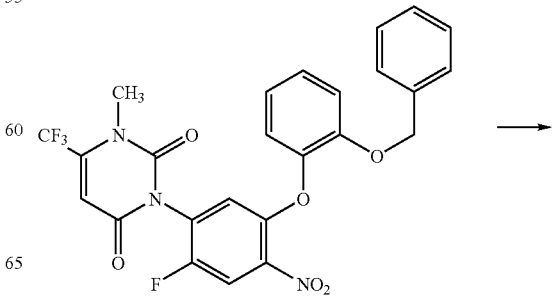

-continued

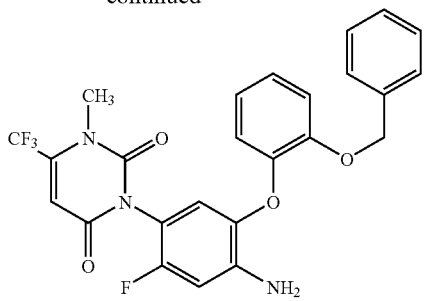

To a mixture of 8.6 g of iron powder, 27 ml of acetic acid, and 2.7 ml of water was added dropwise a solution of 8.6 g of 2-(2-benzyloxyphenoxy)-5-fluoro-4-[3-methyl-2,6-dioxo-4-(trifluoromethyl)-1,2,3,6-tetrahydropyrimidin-1-yl] nitrobenzene in 23 ml of acetic acid, while the temperature of the reaction mixture was kept at 35° C. or lower. After completion of the dropwise addition, the reaction mixture was stirred for 2 hours and then filtered through Celite. The filtrate was diluted with ethyl acetate. The mixture was neutralized with saturated aqueous sodium bicarbonate solution. The organic layer was washed with saturated aqueous sodium chloride solution, dried over anhydrous magnesium sulfate, and then concentrated. The residue was subjected to silica gel column chromatography to give 6.46 g of 2-(2-benzyloxyphenoxy)-5-fluoro4-[3-methyl-2,6-dioxo-4-(trifluoromethyl)-1,2,3,6-tetrahydropyrimidin-1-yl]aniline.

$^1$H-NMR (CDCl$_3$, 250 MHz) δ(ppm): 3.50 (q, 3H, J=1.2 Hz), 5.06 (s, 2H), 6.29 (s, 1H), 6.57 (dd, 1H, J=8.5, 1.6 Hz), 6.9–7.0 (m, 1H), 7.0–7.1 (m, 3H), 7.2–7.4 (m, 6H).

Step 3:

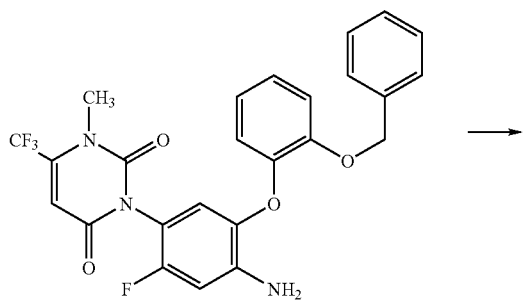

First, 4.46 g of isoamyl nitrite was added dropwise to a mixture of 6.46 g of 2-(2-benzyloxyphenoxy)-5-fluoro-4-[3-methyl-2,6-dioxo-4-(trifluoromethyl)-1,2,3,6-tetrahydropyrimidin-1-yl]aniline, 2.45 g of copper(I) chloride, 5.04 g of copper(II) chloride, and 90 ml of acetonitrile at room temperature, and the mixture was stirred for 1 hour. The reaction mixture was poured into 2% hydrochloric acid, and the mixture was extracted with ethyl acetate. The organic layer was washed with saturated aqueous sodium chloride solution, dried over anhydrous magnesium sulfate, and then concentrated. The residue was subjected to silica gel column chromatography to give 4.6 g of ([2-{2-chloro-4-fluoro-5-[3-methyl-2,6-dioxo-4-(trifluoromethyl)-1,2,3,6-tetrahydropyrimidin-1-yl]phenoxy}phenoxy]methyl)benzene.

m.p.: 50.8° C.

Step 4:

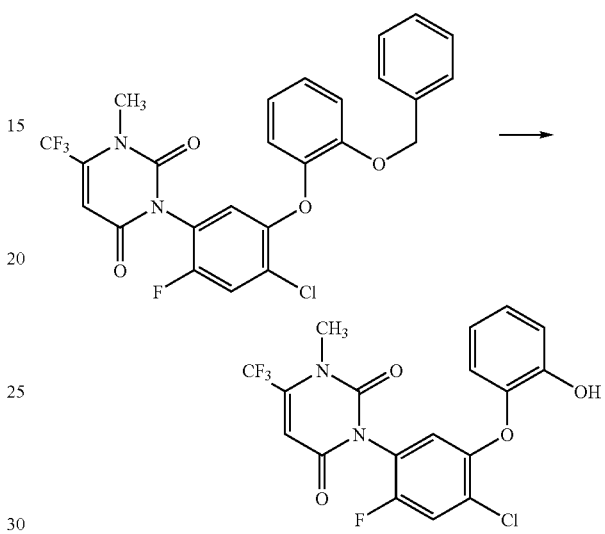

To 4.5 g of ([2-{2-chloro-4-fluoro-5-[3-methyl-2,6-dioxo-4-(trifluoromethyl)-1,2,3,6-tetrahydropyrimidin-1-yl]phenoxy}phenoxy]methyl)benzene were added 230 ml of ethyl acetate and 0.46 g of 10% palladium/carbon, and the mixture was stirred at room temperature under an atmosphere of hydrogen gas for 5 hours. The gas in the atmosphere on the reaction system was replaced with nitrogen gas, and the reaction mixture was filtered through Celite. The filtrate was concentrated to give 3.57 g of 2-{2-chloro-4-fluoro-5-[3-methyl-2,6-dioxo-4-(trifluoromethyl)-1,2,3,6-tetrahydropyrimidin-1-yl]-phenoxy}phenol.

m.p.: 55.4° C.

REFERENCE PRODUCTION EXAMPLE 2

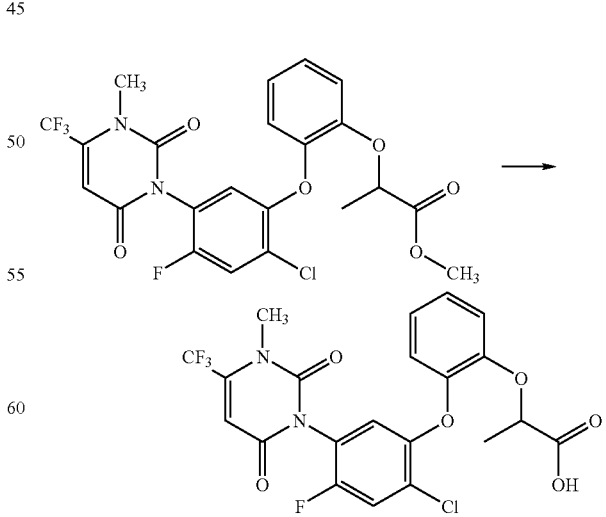

First, 0.365 g of methyl 2-[2-{2-chloro-4-fluoro-5-[3-methyl-2,6-dioxo-4-(trifluoromethyl)-1,2,3,6-tetrahydropyrimidin-1-yl]phenoxy}phenoxy]-propionate was dissolved in 4 ml of 1,4-dioxane, to which a mixed solution of 1 ml of concentrated hydrochloric acid and 1 ml of water was added under stirring, and the mixture was heated and stirred under reflux for 5 hours and 45 minutes. The reaction mixture was then left for cooling, into which ice water was poured, and after addition of ethyl acetate and saturated aqueous sodium chloride solution, the mixture was subjected to phase separation. To the organic layer was added aqueous sodium hydrogencarbonate solution, and the mixture was subjected to phase separation. To the aqueous layer was added aqueous hydrochloric acid solution for acidification, to which ethyl acetate was added, and the mixture was subjected to phase separation. The organic layer was washed with saturated aqueous sodium chloride solution, dried over magnesium sulfate, and then concentrated to give 0.183 g of 2-[2-{2-chloro-4-fluoro-5-[3-methyl-2,6-dioxo-4-(trifluoromethyl)-1,2,3,6-tetrahydropyrimidin-1-yl]phenoxy}phenoxy]propionic acid.

$^1$H-NMR (CDCl$_3$, 250 MHz) δ(ppm): 1.53 (d, 3H, J=6.9 Hz), 3.51 (s, 3H), 4.76–4.83 (m, 1H), 6.32 (d, 1H, J=3.5 Hz), 6.63–6.67 (m, 1H), 7.0–7.1 (m, 2H), 7.1–7.2 (m, 2H), 7.38 (d, 1H, J=9.0 Hz).

REFERENCE PRODUCTION EXAMPLE 3

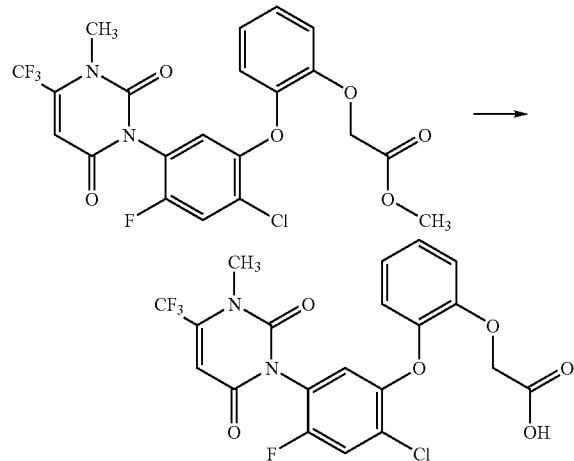

First, 0.4 g of methyl [2-{2-chloro-4-fluoro-5-[3-methyl-2,6-dioxo-4-(trifluoromethyl)-1,2,3,6-tetrahydropyrimidin-1-yl]phenoxy}phenoxy]acetate was dissolved in 4 ml of 1,4-dioxane, to which a mixed solution of 1 ml of concentrated hydrochloric acid and 1 ml of water was added under stirring, and the mixture was heated and stirred under reflux for 12 hours. The reaction mixture was then left for cooling, into which ice water was poured, and after addition of ethyl acetate and saturated aqueous sodium chloride solution, the mixture was subjected to phase separation. To the organic layer was added aqueous sodium hydrogencarbonate solution, and the mixture was subjected to phase separation. To the aqueous layer was added aqueous hydrochloric acid solution for acidification, to which ethyl acetate was added, and the mixture was subjected to phase separation. The organic layer was washed with saturated aqueous sodium chloride solution, dried over magnesium sulfate, and then concentrated to give 0.252 g of [2-{2-chloro-4-fluoro-5-[3-methyl-2,6-dioxo-4-(trifluoromethyl)-1,2,3,6-tetrahydropyrimidin-1-yl]phenoxy}phenoxy]acetic acid.

$^1$H-NMR (CDCl$_3$, 250 MHz) δ(ppm): 3.50 (d, 3H, J=1.2 Hz), 4.66 (s, 2H), 6.31 (s, 1H), 6.69 (d, 1H, J=6.5 Hz), 6.98–7.20 (m, 4H), 7.38 (d, 1H, J=8.8 Hz).

REFERENCE PRODUCTION EXAMPLE 4

Step 1:

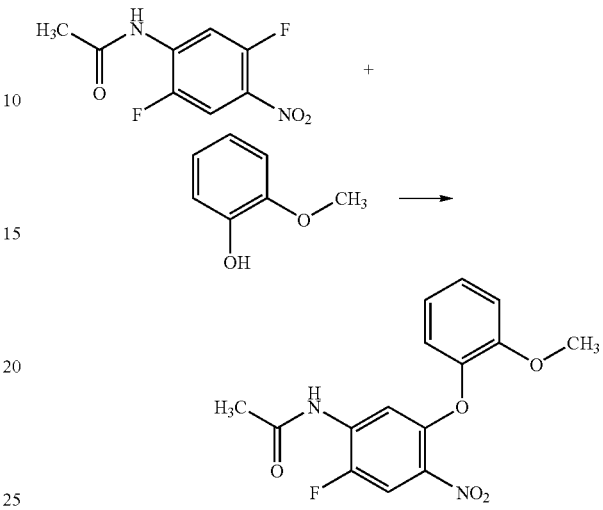

First, 2.73 g of 2-methoxyphenol and 5.5 g of potassium carbonate were added to 20 ml of N,N-dimethylformamide, and the temperature was increased to 60° C. To the mixture was added dropwise a solution consisting of 4.3 g of N-(2,5-difluoro-4-nitrophenyl)acetamide and 30 ml of N,N-dimethylformamide at a temperature of 60° C. to 65° C. After stirring while keeping the temperature for 1 hour, the mixture was cooled to room temperature and then poured into water, and the mixture was extracted with ethyl acetate. The organic layer was washed with diluted hydrochloric acid and water, dried over magnesium sulfate, and then concentrated to give 5.52 g of N-[2-fluoro-5-(2-methoxyphenoxy)-4-nitrophenyl]acetamide.

$^1$H-NMR (250 MHz, CDCl$_3$) δ(ppm): 2.16 (3H, s), 3.78 (3H, s), 6.85–7.22 (4H, m), 7.75–7.83 (1H, br), 7.83 (1H, d, J=10.7 Hz), 8.04 (1H, d, J=6.9 Hz).

Step 2:

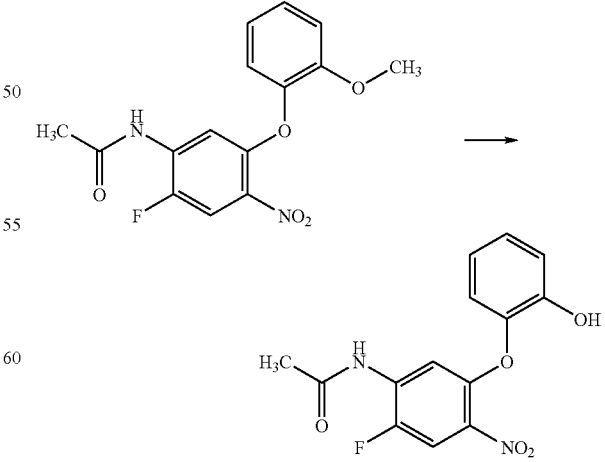

First, 5.4 g of N-[2-fluoro-5-(2-methoxyphenoxy)-4-nitrophenyl]acetamide was dissolved in 50 ml of methylene chloride, to which 4.7 g of boron tribromide was added under ice cooling. After stirring at the same temperature for 2 hours, concentrated hydrochloric acid was added, and the mixture was poured into water, and the mixture was extracted with ethyl acetate. The organic layer was washed with water, dried over magnesium sulfate, and then concentrated. The resulting crystals were washed with t-butyl methyl ether to give 3.2 g of N-[2-fluoro-5-(2-hydroxyphenoxy)-4-nitrophenyl]acetamide.

$^1$H-NMR (300 MHz, CDCl$_3$) δ(ppm): 2.20 (3H, s), 6.33 (1H, bs), 6.86–7.23 (4H, m), 7.63 (1H, bs), 7.81 (1H, d, J=10.3 Hz), 8.34 (1H, d, J=6.7 Hz).

Step 3:

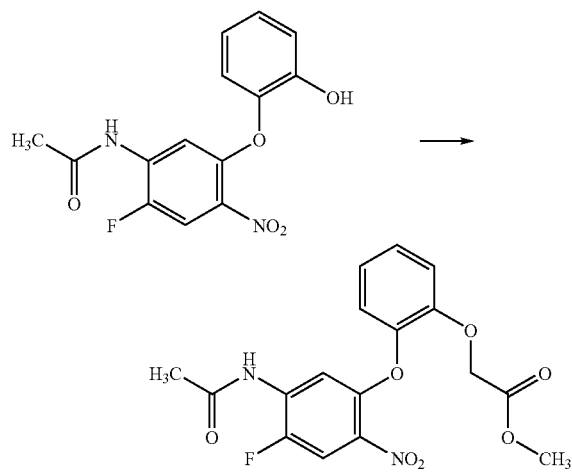

First, 3.02 g of N-[2-fluoro-5-(2-hydroxyphenoxy)-4-nitrophenyl]acetamide was dissolved in 20 ml of N,N-dimethylformamide, to which 1.5 g of potassium carbonate was added, and the mixture was stirred at room temperature for 1 hour. Then, 1.6 g of methyl bromoacetate was added at room temperature. After stirring at the same temperature for 2 hours, the mixture was poured into water, and the mixture was extracted with ethyl acetate. The organic layer was washed with diluted hydrochloric acid and water, dried over magnesium sulfate, and then concentrated. The resulting crystals were washed with t-butyl methyl ether to give 3.01 g of methyl [2-(5-acetylamino-4-fluoro-2-nitrophenoxy)phenoxy]acetate.

$^1$H-NMR (250 MHz, CDCl$_3$) δ(ppm): 2.16 (3H, s), 3.73 (3H, s), 4.62 (2H, s), 6.95–7.26 (4H, m), 7.71 (1H, bs), 7.85 (1H, d, J=10.7 Hz), 8.06 (1H, d, J=6.9 Hz).

Step 4:

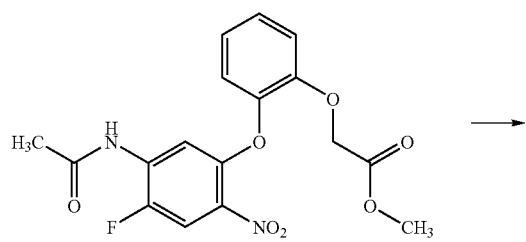

-continued

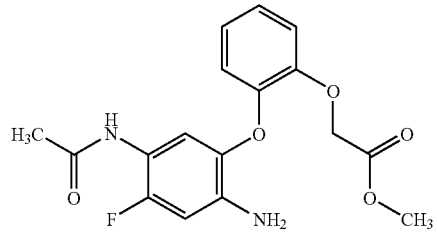

To a mixture of 40 ml of acetic acid and 40 ml of water was added 2.2 g of iron powder, and the temperature was increased to 80° C. To the mixture was added 3.0 g of methyl [2-(5-acetylamino-4-fluoro-2-nitrophenoxy)phenoxy]acetate, and the mixture was heated at reflux for 30 minutes. The mixture was then poured into water, and the mixture was extracted with ethyl acetate. The organic layer was washed with water and saturated aqueous sodium bicarbonate solution, dried over magnesium sulfate, and then concentrated to give 2.01 g of methyl [2-(5-acetylamino-2-amino-4-fluorophenoxy)phenoxy]acetate.

$^1$H-NMR (250 MHz, CDCl$_3$) δ(ppm): 2.11 (3H, s), 3.31–4.15 (2H, br), 3.76 (3H, s), 4.71 (2H, s), 6.54 (1H, d, J=11.9 Hz), 6.90–7.01 (4H, m), 7.17 (1H, bs), 7.69 (1H, d, J=7.5 Hz).

Step 5:

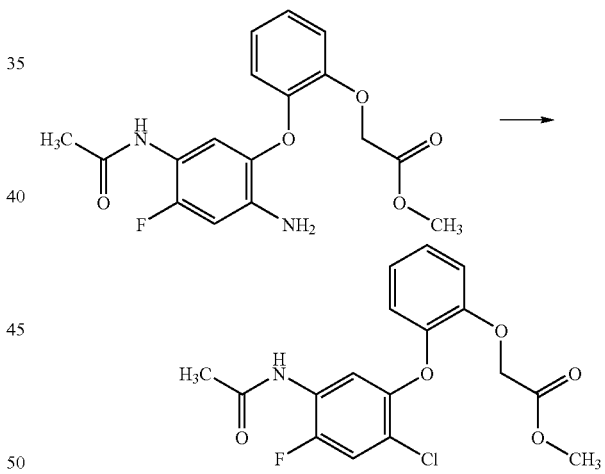

To 30 ml of concentrated hydrochloric acid was added 2.0 g of methyl [2-(5-acetylamino-2-amino-4-fluorophenoxy)phenoxy]acetate, and the mixture was stirred at room temperature for 1 hour. Then, an aqueous solution consisting of 0.42 g of sodium nitrite and 3 ml of water was added under ice cooling. After stirring at the same temperature for 1 hour, 40 ml of t-butyl methyl ether was added and 0.85 g of copper(I) chloride was added. After stirring for 30 minutes, water was added, and the mixture was extracted with t-butyl methyl ether. The organic layer was washed with water, dried over magnesium sulfate, and then concentrated. The residue was subjected to column chromatography (eluent: hexane/ethyl acetate=2/1) to give 0.52 g of methyl [2-(5-acetylamino-2-chloro-4-fluorophenoxy)phenoxy]acetate.

m.p.: 138.9° C.

Step 6:

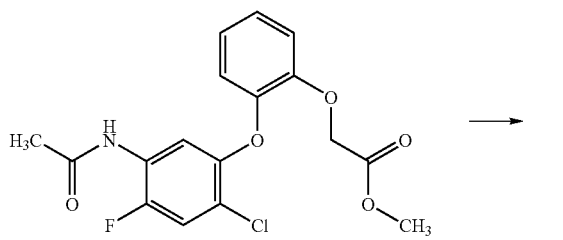

To 10 ml of a methanol solution of a boron trifluoride methanol complex was added 0.25 g of methyl [2-(5-acetylamino-2-chloro-4-fluorophenoxy)phenoxy]acetate, and the mixture was heated and stirred for 3 hours. The reaction mixture was then concentrated. The residue was dissolved in ethyl acetate, and the solution was washed with saturated aqueous sodium bicarbonate solution, dried over magnesium sulfate, and then concentrated to give 0.2 g of methyl [2-(5-amino-2-chloro-4-fluorophenoxy)phenoxy]acetate.

$^1$H-NMR (250 MHz, CDCl$_3$) δ(ppm): 3.74 (3H, s), 3.86 (2H, br), 4.70 (2H, s), 6.36 (1H, d, J=8.21 Hz), 6.83–7.09 (5H, m).

REFERENCE PRODUCTION EXAMPLE 5

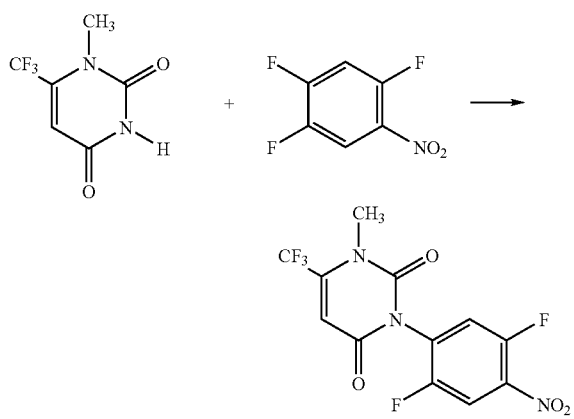

First, 1.77 g of 2,4,5-trifluoronitrobenzene and 1.94 g of 3-methyl-2,6-dioxo-4-(trifluoromethyl)-1,2,3,6-tetrahydropyrimidine were dissolved in 10 ml of dimethylsulfoxide, to which 1.52 g of anhydrous potassium carbonate was added at room temperature, and the mixture was stirred at 80° C. for 1 hour. The reaction mixture was cooled to room temperature and then poured into ice water, and the mixture was extracted with ethyl acetate. The organic layer was washed with saturated aqueous sodium chloride solution, dried over anhydrous magnesium sulfate, and then concentrated. The residue was subjected to silica gel column chromatography to give 1.51 g of 2,5-difluoro-4-[3-methyl-2,6-dioxo-4-(trifluoromethyl)-1,2, 3,6-tetrahydropyrimidin-1-yl]nitrobenzene.

m.p.: 150° C.

REFERENCE PRODUCTION EXAMPLE 6

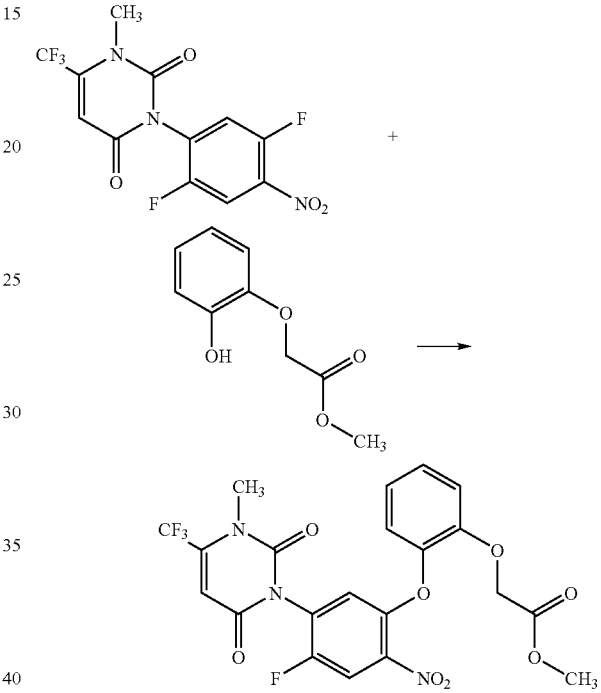

A mixture of 15.16 g of methyl (2-hydroxyphenoxy)acetate, 29.23 g of 2,5-difluoro-4-[3-methyl-2,6-dioxo-4-(trifluoromethyl)-1,2,3,6-tetrahydropyrimidin-1-yl]nitrobenzene, 11.5 g of anhydrous potassium carbonate, and 160 ml of N,N-dimethylformamide was stirred at room temperature for 30 minutes and then at 70° C. for 3 hours. Another 5 g of methyl (2-hydroxyphenoxy)acetate was added, and the mixture was stirred for 1 hour. The reaction mixture was poured into 2% aqueous hydrochloric acid solution, and the mixture was extracted with ethyl acetate. The organic layer was washed with saturated aqueous sodium chloride solution, dried over anhydrous magnesium sulfate, and then concentrated. The residue was subjected to silica gel column chromatography to give 17.8 g of methyl [2-{4-fluoro-5-[3-methyl-2,6-dioxo-4-(trifluoromethyl)-1,2, 3,6-tetrahydropyrimidin-1-yl]-2-nitrophenoxy}phenoxy]acetate.

$^1$H-NMR (CDCl$_3$, 300 MHz) δ(ppm): 3.50 (q, 3H, J=1.0 Hz), 3.70 (s, 3H), 4.63 (s, 2H), 6.28 (s, 1H), 6.88 (d, 1H, J=8.4 Hz), 6.93 (d, 1H, J=6.0 Hz), 7.0–7.1 (m, 1H), 7.1–7.3 (m, 2H), 7.87 (d, 1H, J=8.7 Hz).

REFERENCE PRODUCTION EXAMPLE 7

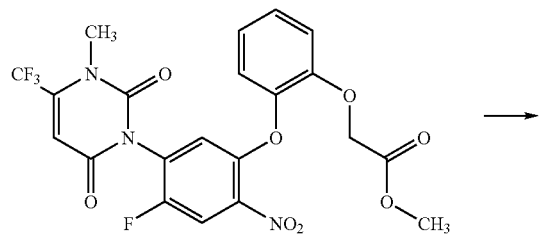

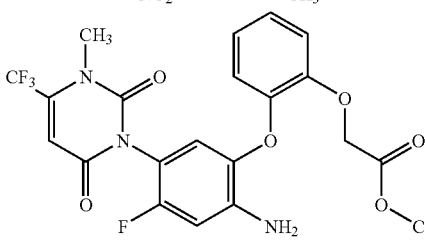

To a mixture of 19 g of iron powder, 60 ml of acetic acid, and 6 ml of water was added dropwise a solution of 19.12 g of methyl [2-{4-fluoro-5-[3-methyl-2,6-dioxo-4-(trifluoromethyl)-1,2,3,6-tetrahydropyrimidin-1-yl]-2-nitrophenoxy}phenoxy]acetate in 60 ml of acetic acid under ice cooling. After completion of the dropwise addition, the temperature was increased to room temperature, and the mixture was stirred for 4 hours. The reaction mixture was filtered through Celite, and the filtrate was diluted with ethyl acetate. The mixture was washed with water, saturated aqueous sodium bicarbonate solution and saturated aqueous sodium chloride solution, dried over anhydrous magnesium sulfate, and then concentrated. The residue was subjected to silica gel chromatography to give 15.16 g of methyl [2-{2-amino-4-fluoro-5-[3-methyl-2,6-dioxo-4-(trifluoromethyl)-1,2,3,6-tetrahydropyrimidin-1-yl]phenoxy}phenoxy]acetate.

$^1$H-NMR (CDCl$_3$, 250 MHz) δ(ppm): 3.51 (q, 3H, J=0.9 Hz), 3.76 (s, 3H), 4.2–4.4 (b, 2H), 4.69 (s, 2H), 6.29 (s, 1H), 6.6–6.7 (m, 2H), 6.9–7.1 (m, 4H).

REFERENCE PRODUCTION EXAMPLE 8

Step 1:

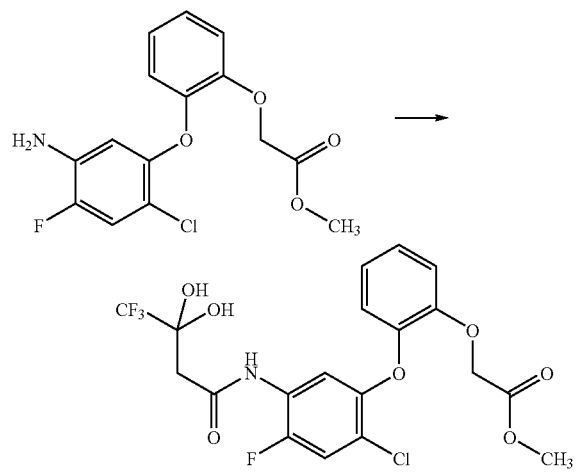

A solution consisting of 4.85 g of methyl [2-(5-amino-2-chloro-4-fluorophenoxy)phenoxy]acetate, 2.88 g of ethyl trifluoroacetoacetate, and 40 ml of toluene was azeotropically distilled for 6 hours, while passing through molecular sieves 5A to remove ethanol. The reaction mixture was cooled, and 50 ml of ethyl acetate was then added. The organic layer was washed with concentrated hydrochloric acid, water and saturated aqueous sodium chloride solution, dried over anhydrous sodium sulfate, and then concentrated under reduced pressure. The residue was washed with hexane to give 5.82 g of crude methyl [2-(5-{3,3-dihydroxy-4,4,4-trifluorobutyryl}-amino-2-chloro-4-fluorophenoxy)phenoxy]acetate.

m.p.: 165.3° C.

Step 2:

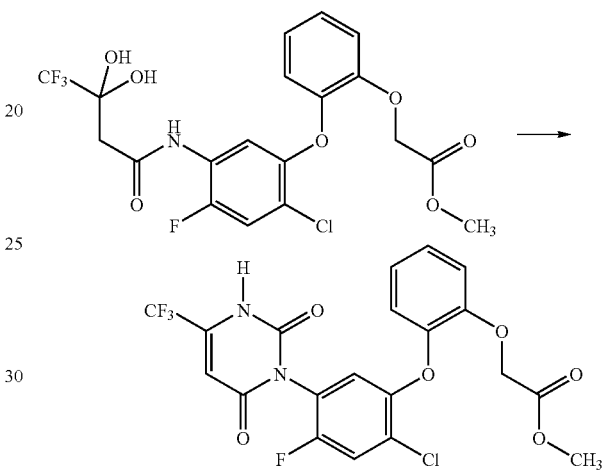

To a solution of 1.0 g of crude methyl [2-(5-{3,3-dihydroxy-4,4,4-trifluorobutyryl}amino-2-chloro-4-fluorophenoxy)phenoxy]acetate and 3 ml of tetrahydrofuran were added 4 ml of acetic acid and 0.87 g of potassium cyanate, and the mixture was stirred at room temperature for 6 hours and then heated at reflux at 120° C. for 2 hours. After cooling, 30 ml of water was added, and the mixture was extracted with ethyl acetate. The organic layer was washed with saturated aqueous sodium bicarbonate solution, water and saturated aqueous sodium chloride solution, dried over anhydrous sodium sulfate, and then concentrated under reduced pressure. The residue was subjected to silica gel column chromatography to give 0.67 g of methyl [2-{2-chloro-5-[2,6-dioxo-4-(trifluoromethyl)-1,2,3,6-tetrahydropyrimidin-1-yl]-4-fluorophenoxy}phenoxy]acetate.

$^1$H-NMR (CDCl$_3$, 250 MHz) δ(ppm): 3.72 (3H, s), 4.65 (2H, s), 6.16 (1H, s)., 6.77 (1H, d, J=6.6 Hz), 6.89–7.15 (4H, m), 7.36 (1H, d, J=8.9 Hz).

REFERENCE PRODUCTION EXAMPLE 9

Step 1:

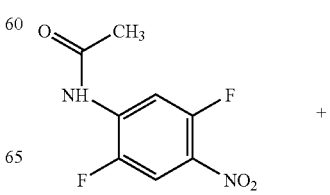

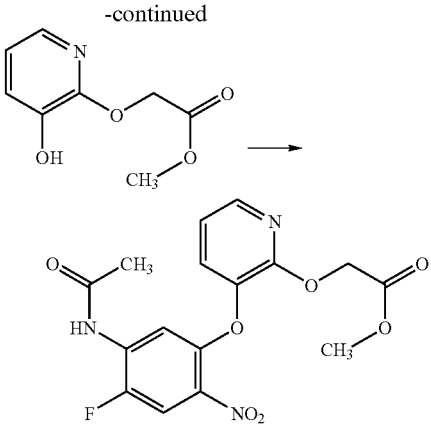

First, 2.08 g of potassium carbonate was added to a solution of 3.0 g of 3-hydroxy-2-(methoxycarbonyl)methoxypyridine, 2.95 g of N-(2,5-difluoro-4-nitrophenyl)acetamide, and 40 ml of N,N-dimethylformamide. The mixture was stirred at 60° C. to 70° C. for 2 hours, cooled to room temperature, and then poured into water. The mixture was extracted with ethyl acetate. The organic layer was washed with saturated aqueous sodium chloride solution, dried over anhydrous magnesium sulfate, and then concentrated to give crude crystals. The crude crystals were washed with diisopropyl ether to give 3.67 g of N-[2-fluoro-5-{2-(methoxycarbonyl)methoxy-3-pyridyloxy}-4-nitrophenyl]acetamide.

$^1$H-NMR (CDCl$_3$, 250 MHz) δ(ppm): 2.21 (s, 3H), 3.72 (s, 3H), 4.90 (s, 2H), 6.96 (dd, 1H, J=7.8, 5.0 Hz), 7.35 (dd, 1H, J=7.8, 1.6 Hz), 7.5–7.6 (b, 1H), 7.90 (d, 1H, J=10.6 Hz), 7.97 (dd, 1H, J=5.0, 1.6 Hz), 8.15 (d, 1H, J=6.8 Hz).

Step 2:

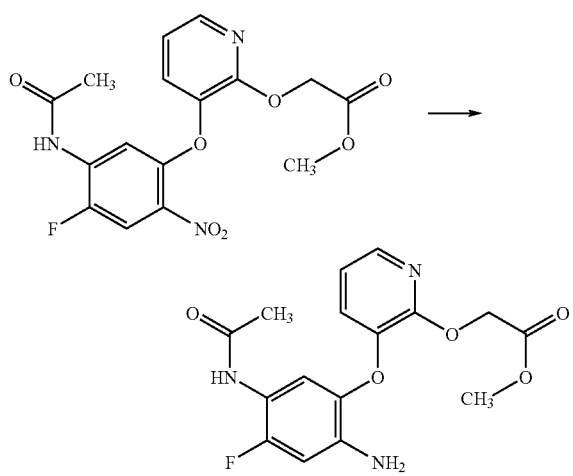

To a mixture of 3.6 g of iron powder, 10 ml of acetic acid, and 1 ml of water was added dropwise a solution of 3.67 g of N-[2-fluoro-5-{2-(methoxycarbonyl)methoxy}-3-pyridyloxy]-4-nitrophenyl]acetamide, 12 ml of acetic acid, and 2 ml of ethyl acetate, while the temperature of the reaction mixture was kept at 45° C. or lower. After completion of the dropwise addition, the reaction mixture was stirred at 40° C. for 1 hour. The reaction mixture was then filtered through Celite, and the filtrate was concentrated. The residue was diluted with saturated aqueous sodium bicarbonate solution, and the mixture was extracted with ethyl acetate. The organic layer was washed with saturated aqueous sodium bicarbonate solution, dried over anhydrous magnesium sulfate, and then concentrated. The residue was washed with diisopropyl ether to give 3.09 g of N-[4-amino-2-fluoro-5-{2-(methoxycarbonyl)methoxy-3-pyridyloxy}phenyl]acetamide.

$^1$H-NMR (CDCl$_3$, 250 MHz) δ(ppm): 2.15 (s, 3H), 3.77 (s, 3H), 3.9–4.1 (b, 2H), 5.03 (s, 2H), 6.56 (d, 1H, J=11.8 Hz), 6.84 (dd, 1H, J=7.9, 5.0 Hz), 7.0–7.2 (b, 1H), 7.14 (dd, 1H, J=7.9, 1.5 Hz), 7.80 (dd, 1H, J=5.0, 1.5 Hz), 7.84 (d, 1H, J=7.6 Hz).

Step 3:

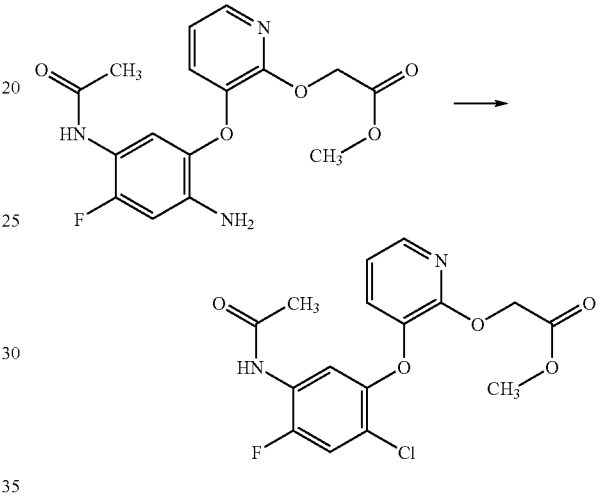

A solution of 2.01 g of isoamyl nitrite in 1 ml of acetonitrile was added dropwise to a mixture of 2.0 g of N-[4-amino-2-fluoro-5-{2-(methoxycarbonyl)methoxy-3-pyridyloxy}phenyl]acetamide, 1.13 g of copper(I) chloride, 2.31 g of copper(II) chloride, and 20 ml of acetonitrile at room temperature, and the mixture was stirred for 1 hour. The reaction mixture was poured into 2% hydrochloric acid, and the mixture was extracted with ethyl acetate. The organic layer was washed with saturated aqueous sodium chloride solution, dried over anhydrous magnesium sulfate, and then concentrated. The residue was subjected to silica gel column chromatography to give 1.04 g of N-[4-chloro-2-fluoro-5-{2-(methoxycarbonyl)methoxy-3-pyridyloxy}phenyl]acetamide.

$^1$H-NMR (CDCl$_3$, 250 MHz) δ(ppm): 2.18 (s, 3H), 3.75 (s, 3H), 4.98 (s, 2H), 6.87 (dd, 1H, J=7.8, 4.9 Hz), 7.08 (dd, 1H, J=7.8, 1.4 Hz), 7.23 (d, 1H, J=10.3 Hz), 7.3–7.4 (b, 1H), 7.86 (dd, 1H, J=4.9, 1.4 Hz) 8.07 (d, 1H, J=7.3 Hz).

Step 4:

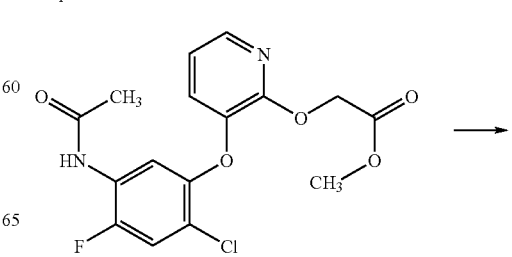

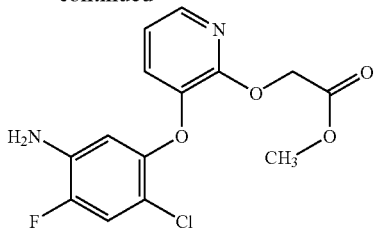

First, 20 ml of a methanol solution of a boron trifluoride methanol complex was mixed with 1.04 g of N-[4-chloro-2-fluoro-5-{2-(methoxycarbonyl)methoxy-3-pyridyloxy}phenyl]acetamide, and the mixture was stirred at 60° C. to 70° C. for 3 hours and then concentrated. The residue was diluted with saturated aqueous sodium bicarbonate solution, and the mixture was extracted with ethyl acetate. The organic layer was washed with saturated aqueous sodium chloride solution, dried over anhydrous magnesium sulfate, and then concentrated. The residue was subjected to column chromatography to give 0.87 g of 4-chloro-2-fluoro-5-{2-(methoxycarbonyl)methoxy-3-pyridyloxy}aniline.

$^1$H-NMR (CDCl$_3$, 250 MHz) δ(ppm): 3.77 (s, 3H), 3.7–3.9 (b, 2H), 5.00 (s, 2H), 6.49 (d, 1H, J=8.2 Hz), 6.88 (dd, 1H, J=7.9, 5.0 Hz), 7.08 (d, 1H, J=10.3 Hz), 7.10 (dd, 1H, J=7.9, 1.6 Hz), 7.87 (dd, 1H, J=5.0, 1.6 Hz).

Step 5:

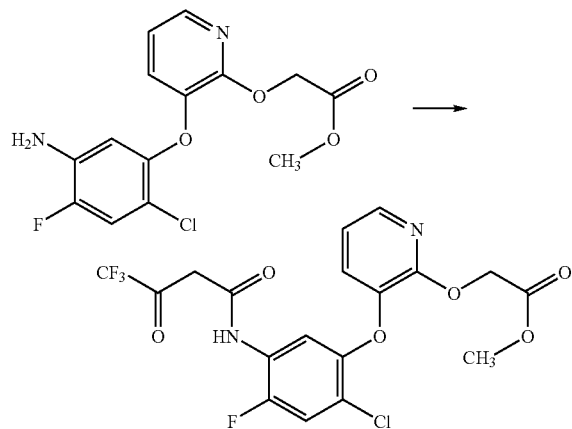

A mixture of 0.5 g of 4-chloro-2-fluoro-5-{2-(methoxycarbonyl)methoxy-3-pyridyloxy}aniline, 0.28 g of ethyl trifluoroacetoacetate, and 10 ml of toluene was azeotropically distilled for 3 hours, while passing through molecular sieves 5A to remove ethanol. After cooling, the reaction mixture was concentrated to give 0.71 g of N-[4-chloro-2-fluoro-5-{2-(methoxycarbonyl)methoxy-3-pyridyloxy}phenyl]trifluoroacetoacetamide.

m.p.: 158.8° C.

Step 6:

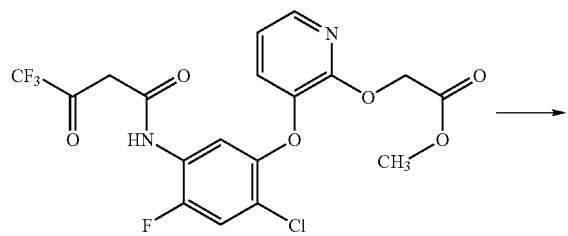

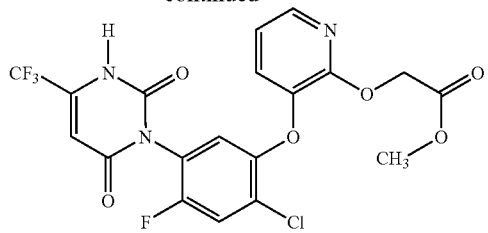

To a mixture of 0.71 g of N-[4-chloro-2-fluoro-5-{2-(methoxycarbonyl)methoxy-3-pyridyloxy}phenyl]trifluoroacetoacetamide and 2 ml of acetic acid was added sodium cyanate, and the mixture was stirred at 50° C. for 1 hour and then at 110° C. for 1.5 hours. After cooling, water was poured into the reaction mixture, and the mixture was extracted with ethyl acetate. The organic layer was washed with saturated aqueous sodium bicarbonate solution, saturated aqueous sodium chloride solution, dried over anhydrous magnesium sulfate, and then concentrated. The residue was subjected to silica gel column chromatography to give 0.30 g of 3-{2-chloro-4-fluoro-5-[2,6-dioxo-4-(trifluoromethyl)-1,2,3,6-tetrahydropyridin-1-yl]phenoxy}-2-(methoxycarbonyl)methoxypyridine.

$^1$H-NMR (CDCl$_3$, 250 MHz) δ(ppm): 3.70 (s, 3H), 4.93 (s, 2/2H), 4.94 (s, 2/2H), 6.19(s, 1H), 6.9–7.0 (m, 2H), 7.3–7.4 (m, 1H), 7.38 (d, 1H, J=8.9 Hz), 7.93 (dd, 1H, J=4.9, 1.6 Hz);

m.p.: 75.3° C.

REFERENCE PRODUCTION EXAMPLE 10

Step 1:

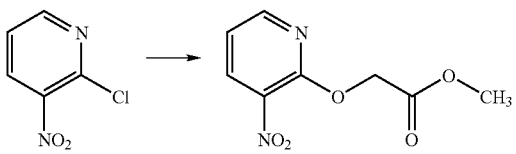

First, 0.4 g of sodium hydride was added to a mixture of 1.59 g of 2-chloro-3-nitropyridine, 0.95 g of methyl glycolate, and 10 ml of 1,4-dioxane at 10° C. After stirring at room temperature for 2 hours, the reaction mixture was poured into ice water, and the mixture was extracted with ethyl acetate. The organic layer was dried over anhydrous magnesium sulfate and then concentrated. The residue was subjected to silica gel column chromatography to give 1.5 g of 2-(methoxycarbonyl)methoxy-3-nitropyridine.

m.p.: 61.5° C.

Step 2:

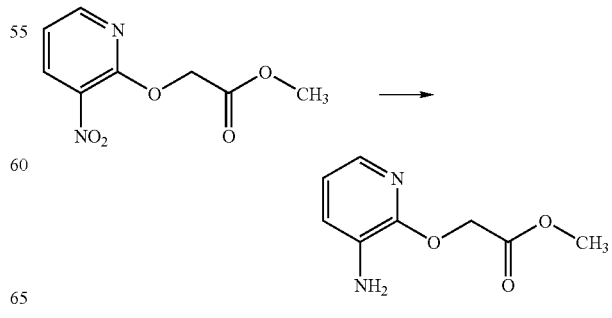

A mixture of 0.3 g of 2-(methoxycarbonyl)methoxy-3-nitropyridine, 20 mg of platinum oxide, and 1.4 ml of ethanol was stirred at room temperature under an atmosphere of hydrogen gas for 3 hours. The gas in the atmosphere on the reaction system was replaced with nitrogen gas, and the reaction mixture was filtered through Celite. The filtrate was concentrated. The residue was subjected to silica gel column chromatography to give 0.22 g of 3-amino-2-(methoxycarbonyl)methoxypyridine.

¹H-NMR (CDCl₃, 250 MHz) δ(ppm): 3.77 (s, 3H), 3.85 (bs, 2H), 4.95 (s, 2H), 6.75 (dd, 1H, J=7.5, 5.0 Hz), 6.91 (dd, 1H, J=7.5, 1.6 Hz), 7.50 (dd, 1H, J=5.0, 1.6 Hz).

Step 3:

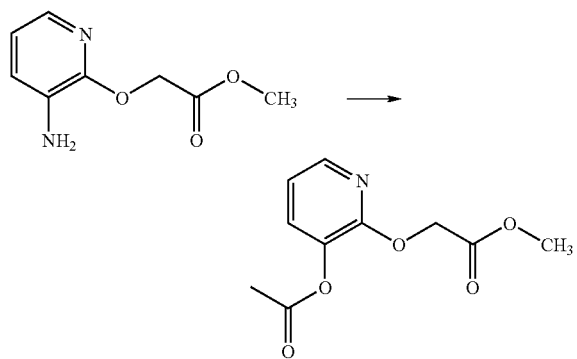

First, 1.6 g of a boron trifluoride diethyl ether complex was added dropwise to a mixture of 1.0 g of 3-amino-2-(methoxycarbonyl)methoxypyridine, 3 ml of 1,2-dimethoxyethane, and 1 ml of dichloromethane at −10° C. After stirring at the same temperature for 10 minutes, a solution of 0.68 g of t-butyl nitrite in 1 ml of 1,2-dimethoxyethane was added dropwise to the reaction mixture at −5° C. or lower. After stirring at the same temperature for 30 minutes, n-pentane was poured into the mixture. The lower one of the two layers separated was dissolved in 5 ml of acetic anhydride, and the solution was stirred at 80° C. for 1 hour. After the solvent was distilled out, the residue was subjected to silica gel chromatography to give 0.45 g of 3-acetoxy-2-(methoxycarbonyl)methoxypyridine.

¹H-NMR (CDCl₃, 250 MHz) δ(ppm): 2.33 (s, 3H), 3.75 (s, 3H), 4.92 (s, 2H), 6.93 (dd, 1H, J=7.7, 5.0 Hz), 7.38 (dd, 1H, J=7.7, 1.6 Hz), 7.97 (dd, 1H, J=5.0, 1.6 Hz).

Step 4:

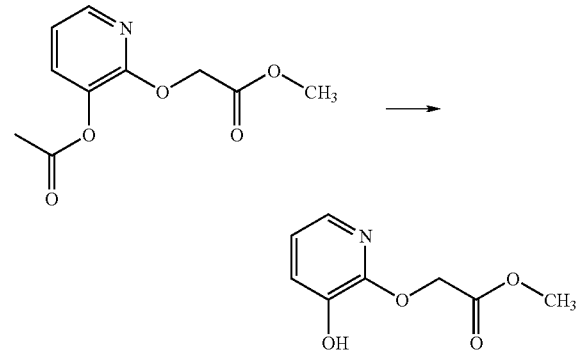

A mixture of 0.1 g of 3-acetoxy-2-(methoxycarbonyl)methoxypyridine, 31 mg of potassium carbonate, and 1 ml of methanol was stirred at room temperature for 3 hours. The reaction mixture was poured into water, and the mixture was extracted with ethyl acetate. The organic layer was dried over anhydrous magnesium sulfate and then concentrated. The residue was subjected to silica gel column chromatography to give 73 mg of 3-hydroxy-2-(methoxycarbonyl)methoxypyridine.

¹H-NMR (CDCl₃, 250 MHz) δ(ppm): 3.78 (s, 3H), 4.98 (s, 2H), 6.84 (dd, 1H, J=7.7, 5.0 Hz), 7.17 (dd, 1H, J=7.7, 1.3 Hz), 7.63 (dd, 1H, J=5.0, 1.3 Hz).

Step 5:

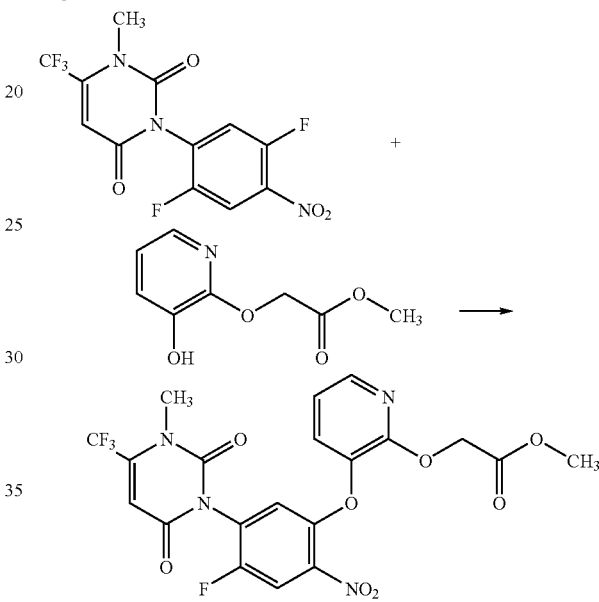

To a mixture of 0.29 g of 3-hydroxy-2-(methoxycarbonyl)methoxypyridine, 0.23 g of 2,5-difluoro-4-[3-methyl-2,6-dioxo-4-(trifluoromethyl)-1,2,3,6-tetrahydropyrimidin-1-yl]nitrobenzene, and 3.2 ml of N,N-dimethylformamide was added 0.11 g of potassium carbonate, and the mixture was stirred at 70° C. for 2 hours. Another 0.12 g of 2,5-difluoro-4-[3-methyl-2,6-dioxo-4-(trifluoromethyl)-1,2,3,6-tetrahydropyrimidin-1-yl]nitrobenzene and another 0.05 g of potassium carbonate were added, and the mixture was stirred at 70° C. for 1 hour. The reaction mixture was cooled to room temperature and then poured into ice water, and the mixture was extracted with ethyl acetate. The organic layer was washed with saturated aqueous sodium chloride solution, dried over anhydrous magnesium sulfate, and then concentrated. The residue was subjected to silica gel column chromatography to give 0.39 g of 3-{4-fluoro-5-[3-methyl-2,6-dioxo-4-(trifluoromethyl)-1,2,3,6-tetrahydropyrimidin-1-yl]-2-nitrophenoxy}-2-(methoxycarbonyl)methoxypyridine.

¹H-NMR (CDCl₃, 250 MHz) δ(ppm): 3.51 (q, 3H, J=1.1 Hz), 3.68 (s, 3H), 4.86 (d, 1H), 4.98 (d, 1H), 6.29 (s, 1H), 6.99 (dd, 1H, J=7.8, 4.9 Hz), 7.11 (d, 1H, J=6.0 Hz), 7.51 (dd, 1H, J=7.8, 1.6 Hz), 7.87 (d, 1H, J=8.6 Hz), 7.99 (dd, 1H, J=4.9, 1.6 Hz).

Step 6:

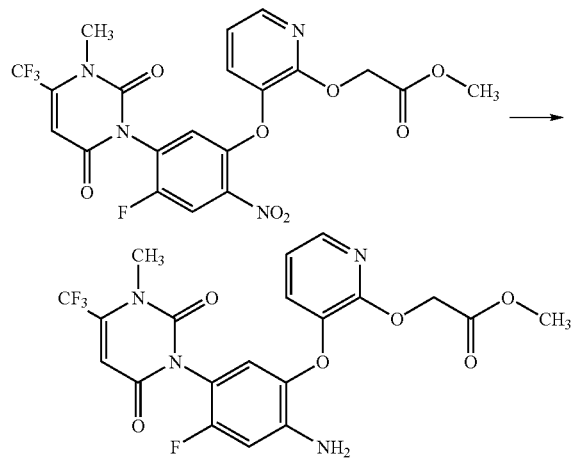

To a mixture of 0.3 g of iron powder, 3 ml of acetic acid, and 0.3 ml of water was added dropwise a solution of 0.30 g of 3-{4-fluoro-5-[3-methyl-2,6-dioxo-4-(trifluoromethyl)-1,2,3,6-tetrahydropyrimidin-1-yl]-2-nitrophenoxy}-2-(methoxycarbonyl)methoxypyridine in 2 ml of acetic acid, while the temperature of the reaction mixture was kept at 35° C. or lower. After completion of the dropwise addition, the mixture was stirred for 2 hours and then filtered through Celite. The filtrate was diluted with ethyl acetate, and the mixture was neutralized with saturated aqueous sodium bicarbonate solution. The organic layer was washed with saturated aqueous sodium chloride solution, dried over anhydrous magnesium sulfate, and then concentrated. The residue was subjected to silica gel column chromatography to give 0.24 g of 3-{2-amino-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine.

$^1$H-NMR (CDCl$_3$, 250 MHz) δ(ppm): 3.52 (s, 3H), 3.74 (s, 3H), 4.29 (bs, 2H), 5.00 (s, 2H), 6.30 (s, 1H), 6.61 (d, 1H, J=11.3 Hz), 6.76 (d, 1H, J=6.8 Hz), 6.86 (dd, 1H, J=7.8, 5.0 Hz), 7.22 (dd, 1H, J=7.8, 1.1 Hz), 7.82 (dd, 1H, J=5.0, 1.1 Hz).

REFERENCE PRODUCTION EXAMPLE 11

Step 1:
First, 0.8 g of sodium hydride was added to a mixture of 3.17 g of 2-chloro-3-nitropyridine, 2.19 g of methyl lactate, and 20 ml of 1,4-dioxane at 10° C., and the mixture was stirred at room temperature for 1.5 hours. The reaction mixture was poured into ice water, and the mixture was extracted with ethyl acetate. The organic layer was dried over anhydrous magnesium sulfate and then concentrated. The residue was subjected to silica gel column chromatography to give 3.3 g of 2-{1-(methoxycarbonyl)ethoxy}-3-nitropyridine.

$^1$H-NMR (CDCl$_3$, 300 MHz) δ(ppm): 1.70 (d, 3H, J=7.0 Hz), 3.74 (s, 3H), 5.46 (q, 1H, J=7.0 Hz), 7.07 (dd, 1H, J=7.8, 5.0 Hz), 8.2–8.4 (m, 2H).

Step 2:
A mixture of 1.7 g of 2-{1-(methoxycarbonyl)ethoxy}-3-nitropyridine, 102 mg of platinum oxide, and 7.5 ml of ethanol was stirred at room temperature under an atmosphere of hydrogen gas for 3.5 hours. The gas in the atmosphere on the reaction system was replaced with nitrogen gas, and the reaction mixture was filtered through Celite. The filtrate was concentrated. The residue was subjected to silica gel column chromatography to give 1.16 g of 3-amino-2-{1-(methoxycarbonyl)ethoxy}pyridine.

$^1$H-NMR (CDCl$_3$, 300 MHz) δ(ppm): 1.63 (d, 3H, J=6.8 Hz), 3.74 (s, 3H), 3.84 (bs, 2H), 5.38 (d, 1H, J=6.8 Hz), 6.72 (dd, 1H, J=7.7, 5.0 Hz), 6.90 (dd, 1H, J=7.7, 1.4 Hz), 7.48 (dd, 1H, J=5.0, 1.4 Hz).

Step 3:
First, 1.5 ml of a boron trifluoride diethyl ether complex was added dropwise to a mixture of 1.1 g of 3-amino-2-{1-(methoxycarbonyl)ethoxy}-pyridine, 1 ml of 1,2-dimethoxyethane, and 1 ml of dichloroethane at –10° C. After stirring at the same temperature for 10 minutes, a solution of 0.8 ml of t-butyl nitrite in 1 ml of 1,2-dimethoxyethane was added dropwise to the reaction mixture at –5° C. or lower. After stirring at the same temperature for 30 minutes, n-pentane was poured into the mixture. The lower one of the two layers separated was dissolved in acetic anhydride, and the solution was stirred at 70° C. for 1 hour. After the solvent was distilled out, the residue was subjected to silica gel chromatography to give 0.34 g of 3-acetoxy-2-{1-(methoxycarbonyl)ethoxy}pyridine.

$^1$H-NMR (CDCl$_3$, 300 MHz) δ(ppm): 1.60 (d, 1H, J=7.0 Hz), 2.33 (s, 3H), 3.73 (s, 3H), 5.34 (q, 1H, J=7.0 Hz), 6.91 (dd, 1H, J=7.6, 5.0 Hz), 7.36 (dd, 1H, J=7.6, 1.5 Hz), 7.97 (dd, 1H, J=5.0, 1.5 Hz).

Step 4:
A mixture of 0.34 g of 3-acetoxy-2-{1-(methoxycarbonyl)ethoxy}pyridine, 0.11 g of potassium carbonate, and 2 ml of methanol was stirred at room temperature for 1 hour. The reaction mixture was poured into water, and the mixture was extracted with ethyl acetate. The organic layer was dried over anhydrous magnesium sulfate and then concentrated. The residue was subjected to silica gel column chromatography to give 198 mg of 3-hydroxy-2-{1-(methoxycarbonyl)ethoxy}pyridine.

$^1$H-NMR (CDCl$_3$, 300 MHz) δ(ppm): 1.64 (d, 1H, J=7.0 Hz), 3.75 (s, 3H), 5.45 (q, 1H, J=7.0 Hz), 6.0–6.2 (bs, 1H), 6.83 (dd, 1H, J=7.7, 5.0 Hz), 7.15 (dd, 1H, J=7.7, 1.5 Hz), 7.63 (dd, 1H, J=5.0, 1.5 Hz).

Step 5:
To a mixture of 0.18 g of 3-hydroxy-2-{1-(methoxycarbonyl)ethoxy}-pyridine, 0.19 g of 2,5-difluoro-4-[3-methyl-2,6-dioxo-4-(trifluoromethyl)-1,2,3,6-tetrahydropyrimidin-1-yl]nitrobenzene, and 2.0 ml of N,N-dimethylformamide was added 90 mg of potassium carbonate, and the mixture was stirred at 70° C. for 3 hours. The reaction mixture was cooled to room temperature and then poured into ice water, and the mixture was extracted with ethyl acetate. The organic layer was washed with saturated aqueous sodium chloride solution, dried over anhydrous magnesium sulfate, and then concentrated. The residue was subjected to silica gel column chromatography to give 0.21 g of 3-{4-fluoro-5-[3-methyl-2,6-dioxo-4-(trifluoromethyl)-1,2,3,6-tetrahydropyrimidin-1-yl]-2-nitrophenoxy}-2-{1-(methoxycarbonyl)ethoxy}pyridine as a mixture of diastereoisomers.

$^1$H-NMR (CDCl$_3$, 300 MHz) δ(ppm): 1.45 (d, 3/2H, J=7.1 Hz), 1.46 (d, 3/2H, J=7.1 Hz), 3.49 (s, 3/2H), 3.51 (s, 3/2H), 3.66 (s, 3H), 5.29 (q, 1/2H, J=7.1 Hz), 5.31 (q, 1/2H, J=7.1 Hz), 6.28 (s, 1/2H), 6.30 (s, 1/2H), 6.9–7.0 (m, 1H), 7.10 (d, 1/2H, J=6.1 Hz), 7.17 (d, 1/2H, J=6.1 Hz), 7.4–7.6 (m, 1H), 7.8–7.9 (m, 1H), 7.9–8.0 (m, 1H).

Step 6:
To a mixture of 0.21 g of iron powder, 3 ml of acetic acid, and 0.3 ml of water was added dropwise a solution of 3-{4-fluoro-5-[3-methyl-2,6-dioxo-4-(trifluoromethyl)-1,2,3,6-tetrahydropyrimidin-1-yl]-2-nitrophenoxy}-2-{1-(methoxycarbonyl)ethoxy}pyridine in 1.2 ml of acetic acid, while the temperature of the reaction mixture was kept at 35° C. or lower. After completion of the dropwise addition, the mixture was stirred for 1 hour and then filtered through Celite. The filtrate was diluted with ethyl acetate. The mixture was neutralized with saturated aqueous sodium bicarbonate solution. The organic layer was washed with saturated aqueous sodium chloride solution, dried over anhydrous magnesium sulfate, and then concentrated. The residue was subjected to silica gel chromatography to give 0.16 g of 3-{2-amino-4-fluoro-5-[3-methyl-2,6-dioxo-4-(trifluoromethyl)-1,2,3,6-tetrahydropyrimidin-1-yl]phenoxy}-2-{1-(methoxycarbonyl)ethoxy}pyridine as a mixture of diastereoisomers.

$^1$H-NMR (CDCl$_3$, 300 MHz) δ(ppm): 1.61 (d, 3H, J=7.1 Hz), 3.52 (s, 3H), 3.72 (s, 3H), 4.28 (bs, 2H), 5.40 (q, 1/2H, J=7.1 Hz), 5.41 (q, 1/2H, J=7.1 Hz), 6.30 (s, 1H), 6.62 (d, 1H, J=10.9 Hz), 6.7–6.8 (m, 1H), 6.8–6.9 (m, 1H), 7.2–7.3 (m, 1H), 7.7–7.9 (m, 1H).

REFERENCE PRODUCTION EXAMPLE 12

Step 1:

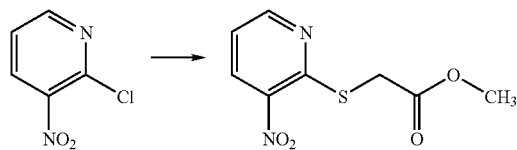

First, 0.8 g of sodium hydride was added to a mixture of 3.17 g of 2-chloro-3-nitropyridine, 2.12 g of methyl thioglycolate, and 20 ml of tetrahydrofuran at 0° C. After stirring at room temperature for 2 hours, the reaction mixture was poured into ice water, and the mixture was extracted with ethyl acetate. The organic layer was dried over anhydrous magnesium sulfate and then concentrated. The residue was washed with diisopropyl ether and hexane to give 3.1 g of 2-(methoxycarbonyl)methylthio-3-nitropyridine.

$^1$H-NMR (CDCl$_3$, 300 MHz) δ(ppm): 3.75 (s, 3H), 3.98 (s, 2H), 7.24 (dd, 1H, J=8.0, 4.8 Hz), 8.54 (dd, 1H, J=8.0, 1.8 Hz), 8.66 (dd, 1H, J=4.8, 1.8 Hz).

Step 2:

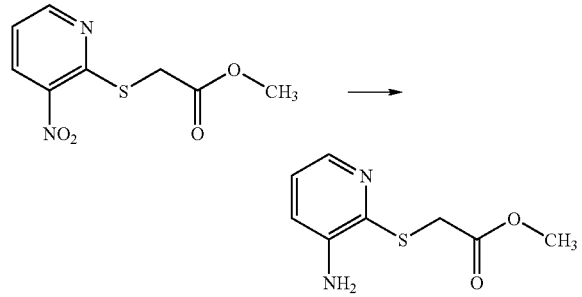

A mixture of 3.0 g of 2-(methoxycarbonyl)methylthio-3-nitropyridine, 180 mg of platinum oxide, and 14 ml of ethanol was stirred at room temperature under an atmosphere of hydrogen gas for 3 hours. The gas in the atmosphere on the reaction system was placed with nitrogen gas, and the reaction mixture was filtered through Celite. The filtrate was concentrated. The residue was subjected to silica gel column chromatography to give 2.54 g of 3-amino-2-(methoxycarbonyl)methylthiopyridine.

$^1$H-NMR (CDCl$_3$, 250 MHz) δ(ppm): 3.73 (s, 3H), 4.03 (s, 2H), 6.2–6.4 (b, 1H), 7.06 (dd, 1H, J=8.0, 4.9 Hz), 7.1–7.2 (bs, 1H), 7.47 (dd, 1H, J=8.0, 1.4 Hz), 8.05 (dd, 1H, J=4.9, 1.4 Hz).

Step 3:

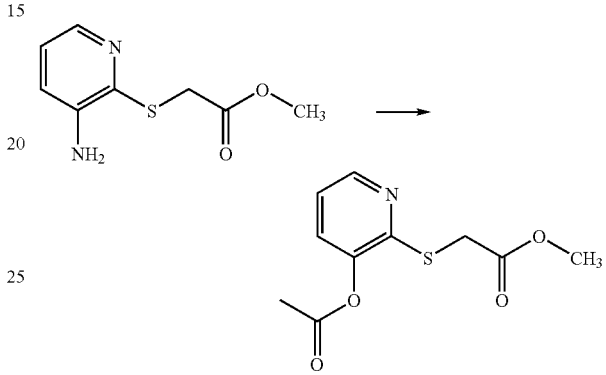

First, 1.92 g of trifluoromethanesulfonic acid was added dropwise to a mixture of 2.54 g of 3-amino-2-(methoxycarbonyl)methylthiopyridine, 6 ml of 1,2-dimethoxyethane, and 2 ml of dichloromethane at −10° C. After stirring at the same temperature for 10 minutes, a solution of 1.59 g of t-butyl nitrite in 1 ml of 1,2-dimethoxyethane was added dropwise to the reaction mixture at −5° C. or lower. After stirring at the same temperature for 30 minutes, n-pentane was poured into the mixture. The lower one of the two layers separated was dissolved in 3 ml of acetic anhydride, and the solution was stirred at 50° C. to 70° C. for 1 hour. The reaction mixture was cooled to room temperature and then poured into water, and the mixture was extracted with t-butyl methyl ether. The organic layer was washed with saturated aqueous sodium hydrogencarbonate solution and saturated aqueous sodium chloride solution, dried over anhydrous magnesium sulfate, and then concentrated. The residue was subjected to silica gel chromatography to give 0.48 g of 3-acetoxy-2-(methoxycarbonyl)methylthiopyridine.

$^1$H-NMR (CDCl$_3$, 250 MHz) δ(ppm): 2.36 (s, 3H), 3.74 (s, 3H), 4.00 (s, 2H), 7.07 (dd, 1H, J=8.0, 4.7 Hz), 7.37 (dd, 1H, J=8.0, 1.5 Hz), 8.29 (dd, 1H, J=4.7, 1.5 Hz).

Step 4:

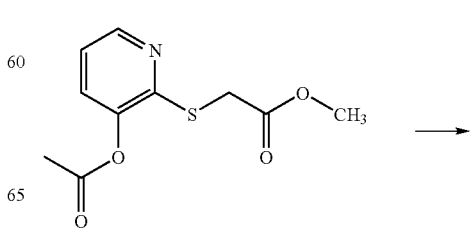

-continued

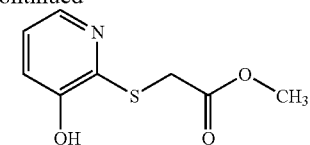

5

A mixture of 0.48 g of 3-acetoxy-2-(methoxycarbonyl) methylthiopyridine, 0.15 g of potassium carbonate, and 3 ml of methanol was stirred at room temperature for 3 hours. The reaction mixture was poured into water, and the mixture was extracted with ethyl acetate. The organic layer was dried over anhydrous magnesium sulfate and then concentrated. The residue was subjected to silica gel column chromatography to give 0.26 g of 3-hydroxy-2-(methoxycarbonyl) methylthiopyridine.

$^1$H-NMR (CDCl$_3$, 250 MHz) δ(ppm): 3.74 (s, 3H), 3.92 (s, 2H), 7.02 (dd, 1H, J=8.1, 4.6 Hz), 7.13 (d, 1H, J=8.1 Hz), 8.06 (d, 1H, J=4.6 Hz).

Step 5:

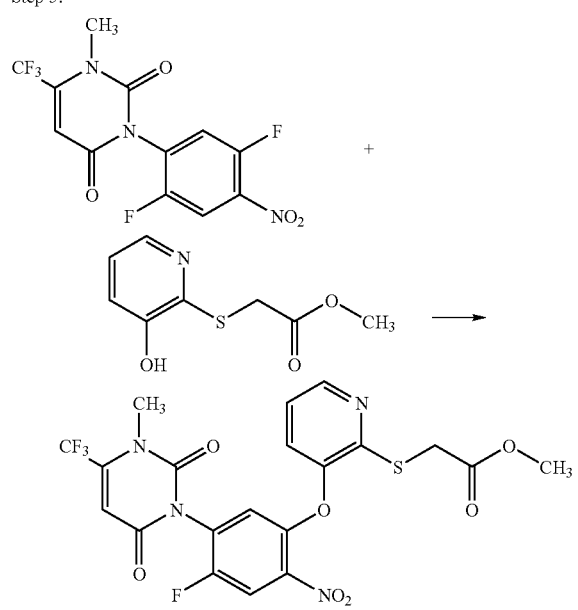

To a mixture of 0.26 g of 3-hydroxy-2-(methoxycarbonyl) methylthiopyridine, 0.38 g of 2,5-difluoro-4-[3-methyl-2,6-dioxo-4-(trifluoromethyl)-1,2,3,6-tetrahydropyrimidin-1-yl] nitrobenzene, and 2 ml of N,N-dimethylformamide was added 0.17 g of potassium carbonate, and the mixture was stirred at 70° C. for 2 hours. The reaction mixture was cooled to room temperature and then poured into ice water, and the mixture was extracted with ethyl acetate. The organic layer was washed with saturated aqueous sodium chloride solution, dried over anhydrous magnesium sulfate, and then concentrated. The residue was subjected to silica gel column chromatography to give 0.49 g of 3-{4-fluoro-5-[3-methyl-2,6-dioxo-4-(trifluoromethyl)-1,2,3,6-tetrahydropyrimidin-1-yl]-2-nitrophenoxy}-2-(methoxycarbonyl) methylthiopyridine.

$^1$H-NMR (CDCl$_3$, 300 MHz) δ(ppm): 3.54 (s, 3H), 3.73 (s, 3H), 4.01 (s, 2H), 6.33 (s, 1H), 7.0–7.1 (m, 2H), 7.18 (dd, 1H, J=7.8, 1.3 Hz), 7.92 (d, 1H, J=8.5 Hz), 8.28 (dd, 1H, J=4.4, 1.3 Hz).

Step 6:

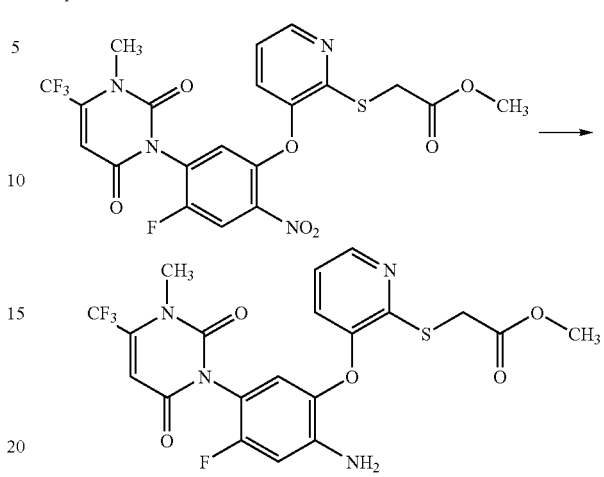

To a mixture of 0.5 g of iron powder, 1.5 ml of acetic acid, and 0.15 ml of water was added dropwise a solution of 0.41 g of 3-{4-fluoro-5-[3-methyl-2,6-dioxo-4-(trifluoromethyl)-1,2,3,6-tetrahydropyrimidin-1-yl]-2-nitrophenoxy}-2-(methoxycarbonyl)methylthiopyridine in 1 ml of acetic acid, while the temperature of the reaction mixture was kept at 35° C. or lower. After completion of the dropwise addition, the reaction mixture was stirred for 2 hours and then filtered through Celite. The filtrate was diluted with ethyl acetate. The mixture was neutralized with saturated aqueous sodium bicarbonate solution. The organic layer was washed with saturated aqueous sodium chloride solution, dried over anhydrous magnesium sulfate, and then concentrated. The residue was subjected to silica gel column chromatography to give 0.36 g of 3-{2-amino-4-fluoro-5-[3-methyl-2,6-dioxo-4-(trifluoromethyl)-1,2,3,6-tetrahydropyrimidin-1-yl] phenoxy}-2-(methoxycarbonyl)methylthiopyridine.

$^1$H-NMR (CDCl$_3$, 250 MHz) δ(ppm): 3.53 (s, 3H), 3.75 (s, 3H), 4.02 (s, 2H), 4.18 (bs, 2H), 6.32 (s, 1H), 6.66 (d, 1H, J=10.7 Hz), 6.82 (d, 1H, J=6.7 Hz), 6.95 (dd, 1H, J=8.4, 4.9 Hz), 7.03 (dd, 1H, J=8.4, 1.4 Hz), 8.14 (dd, 1H, J=4.9, 1.4 Hz).

Specific examples of compounds (I) are shown below.

TABLE 1

Compounds of formula (I-a) (compound a-1 to compound a-124)

(I-a)

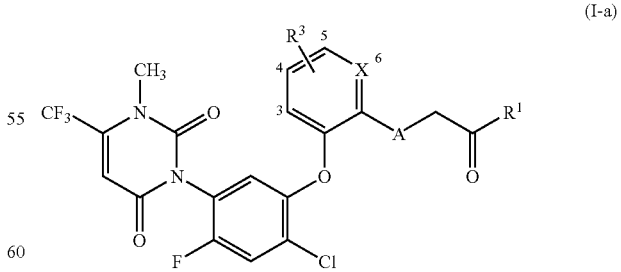

| Compound No. | A | X | R$^3$ | R$^1$ |
|---|---|---|---|---|
| a-1 | O | CH | H | OH |
| a-2 | O | N | H | OH |
| a-3 | S | CH | H | OH |
| a-4 | S | N | H | OH |

TABLE 1-continued

Compounds of formula (I-a) (compound a-1 to compound a-124)

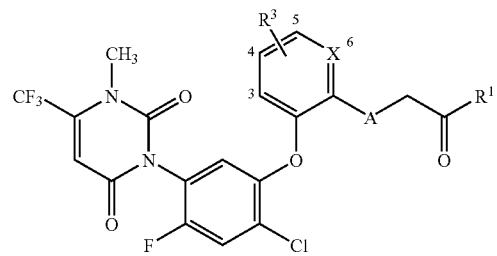

(I-a)

| Compound No. | A | X | R³ | R¹ |
|---|---|---|---|---|
| a-5 | O | CH | H | OCH₃ |
| a-6 | O | N | H | OCH₃ |
| a-7 | S | CH | H | OCH₃ |
| a-8 | S | N | H | OCH₃ |
| a-9 | O | CH | H | OCH₂CH₃ |
| a-10 | O | N | H | OCH₂CH₃ |
| a-11 | S | CH | H | OCH₂CH₃ |
| a-12 | S | N | H | OCH₂CH₃ |
| a-13 | O | CH | H | OCH₂CH₂CH₃ |
| a-14 | O | N | H | OCH₂CH₂CH₃ |
| a-15 | S | CH | H | OCH₂CH₂CH₃ |
| a-16 | S | N | H | OCH₂CH₂CH₃ |
| a-17 | O | CH | H | OCH₂CH₂CH₂CH₃ |
| a-18 | O | N | H | OCH₂CH₂CH₂CH₃ |
| a-19 | O | CH | H | OCH₂CH₂CH₂CH₂CH₃ |
| a-20 | O | N | H | OCH₂CH₂CH₂CH₂CH₃ |
| a-21 | O | CH | H | OCH₂CH=CH₂ |
| a-22 | O | N | H | OCH₂CH=CH₂ |
| a-23 | O | CH | H | OCH(CH₃)₂ |
| a-24 | O | N | H | OCH(CH₃)₂ |
| a-25 | O | CH | H | OCH₂C≡CH |
| a-26 | O | N | H | OCH₂C≡CH |
| a-27 | O | CH | H | O(c-C₅H₉) |
| a-28 | O | N | H | O(c-C₅H₉) |
| a-29 | O | CH | H | O(c-C₆H₁₁) |
| a-30 | O | N | H | O(c-C₆H₁₁) |
| a-31 | O | CH | N | OCH₂CO₂CH₃ |
| a-32 | O | N | H | OCH₂CO₂CH₃ |
| a-33 | O | CH | H | OC(CH₃)₂CO₂CH₃ |
| a-34 | O | N | H | OC(CH₃)₂CO₂CH₃ |
| a-35 | O | CH | H | NH₂ |
| a-36 | O | N | H | NH₂ |
| a-37 | S | CH | H | NH₂ |
| a-38 | S | N | H | NH₂ |
| a-39 | O | CH | H | NHCH₃ |
| a-40 | O | N | H | NHCH₃ |
| a-41 | S | CH | H | NHCH₃ |
| a-42 | S | N | H | NHCH₃ |
| a-43 | O | CH | H | NHCH₂CH₃ |
| a-44 | O | N | H | NHCH₂CH₃ |
| a-45 | S | CH | H | NHCH₂CH₃ |
| a-46 | S | N | H | NHCH₂CH₃ |
| a-47 | O | CH | H | NHCH₂CH₂CH₃ |
| a-48 | O | N | H | NHCH₂CH₂CH₃ |
| a-49 | S | CH | H | NHCH₂CH₂CH₃ |
| a-50 | S | N | H | NHCH₂CH₂CH₃ |
| a-51 | O | CH | H | NHCH₂CH₂CH₂CH₃ |
| a-52 | O | N | H | NHCH₂CH₂CH₂CH₃ |
| a-53 | O | CH | H | NHCH₂CH₂CH₂CH₂CH₃ |
| a-54 | O | N | H | NHCH₂CH₂CH₂CH₂CH₃ |
| a-55 | O | CH | H | NHCH₂CH=CH₂ |
| a-56 | O | N | H | NHCH₂CH=CH₂ |
| a-57 | O | CH | H | NHCH(CH₃)₂ |
| a-58 | O | N | H | NHCH(CH₃)₂ |
| a-59 | O | CH | H | NHCH₂C≡CH |
| a-60 | O | N | H | NHCH₂C≡CH |
| a-61 | O | CH | H | NH(c-C₅H₉) |
| a-62 | O | N | H | NH(c-C₅H₉) |
| a-63 | O | CH | H | NH(c-C₆H₁₁) |
| a-64 | O | N | H | NH(c-C₆H₁₁) |
| a-65 | O | CH | H | NHCH₂CO₂CH₃ |
| a-66 | O | N | H | NHCH₂CO₂CH₃ |
| a-67 | O | CH | H | NHC(CH₃)₂CO₂CH₃ |
| a-68 | O | N | H | NHC(CH₃)₂CO₂CH₃ |
| a-69 | NH | CH | H | OH |
| a-70 | NH | N | H | OH |
| a-71 | NH | CH | H | OH |
| a-72 | NH | N | H | OH |
| a-73 | NH | CH | H | OCH₃ |
| a-74 | NH | N | H | OCH₃ |
| a-75 | NH | CH | H | OCH₃ |
| a-76 | NH | N | H | OCH₃ |
| a-77 | NH | CH | H | OCH₂CH₃ |
| a-78 | NH | N | H | OCH₂CH₃ |
| a-79 | NH | CH | N | OCH₂CH₃ |
| a-80 | NH | N | H | OCH₂CH₃ |
| a-81 | NH | CH | H | OCH₂CH₂CH₃ |
| a-82 | NH | N | H | OCH₂CH₂CH₃ |
| a-83 | NH | CH | H | OCH₂CH₂C₃ |
| a-84 | NH | N | H | OCH₂CH₂CH₃ |
| a-85 | NH | CH | H | OCH₂CH₂CH₂CH₃ |
| a-86 | NH | N | H | OCH₂CH₂CH₂CH₃ |
| a-87 | NH | CH | H | OCH₂CH₂CH₂CH₂CH₃ |
| a-88 | NH | N | H | OCH₂CH₂CH₂CH₂CH₃ |
| a-89 | NH | CH | H | OCH₂CH=CH₂ |
| a-90 | NH | N | H | OCH₂CH=CH₂ |
| a-91 | O | CH | H | ONHCH₃ |
| a-92 | O | N | H | ONHCH₃ |
| a-93 | O | CH | H | ONHCH₂CH₃ |
| a-94 | O | N | H | ONHCH₂CH₃ |
| a-95 | O | CH | H | ON(CH₃)₂ |
| a-96 | O | N | H | ON(CH₃)₂ |
| a-97 | O | CH | H | ON=C(CH₃)₂ |
| a-98 | O | N | H | ON=C(CH₃)₂ |
| a-99 | O | CH | H | N(CH₂CH₃)₂ |
| a-100 | O | N | H | N(CH₂CH₃)₂ |
| a-101 | O | CH | H | N(CH₃)(CH₂CH₃) |
| a-102 | O | N | H | N(CH₃)(CH₂CH₃) |
| a-103 | O | CH | H | NHOCH₃ |
| a-104 | O | N | H | NHOCH₃ |
| a-105 | O | CH | H | NHOCH₂CH₃ |
| a-106 | O | N | H | NHOCH₂CH₃ |
| a-107 | O | CH | 5-Cl | OCH₃ |
| a-108 | O | N | 5-Cl | OCH₃ |
| a-109 | S | CH | 5-Cl | OCH₃ |
| a-110 | S | N | 5-Cl | OCH₃ |
| a-111 | O | CH | 5-Cl | OCH₂CH₃ |
| a-112 | O | N | 5-Cl | OCH₂CH₃ |
| a-113 | O | CH | 5-F | OCH₃ |
| a-114 | O | N | 5-F | OCH₃ |
| a-115 | O | CH | 5-CH₃ | OCH₃ |
| a-116 | O | N | 5-CH₃ | OCH₃ |
| a-117 | O | CH | 5-OCH₃ | OCH₃ |
| a-118 | O | N | 5-OCH₃ | OCH₃ |
| a-119 | O | CH | 5-OCH₃ | OCH₂CH₃ |
| a-120 | O | N | 5-OCH₃ | OCH₂CH₃ |
| a-121 | O | CH | H | O-tert-C₄H₉ |
| a-122 | O | N | H | O-tert-C₄H₉ |
| a-123 | O | CH | H | I-iso-C₄H₉ |
| a-124 | O | N | H | O-iso-C₄H₉ |

TABLE 2

Compounds of formula (I-b) (compound b-1 to compound b-124)

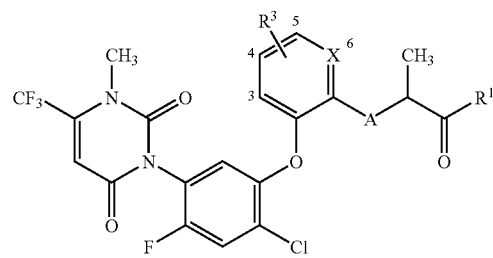

(I-b)

| Compound No. | A | X | R³ | R¹ |
|---|---|---|---|---|
| b-1 | O | CH | H | OH |
| b-2 | O | N | H | OH |
| b-3 | S | CH | H | OH |
| b-4 | S | N | H | OH |
| b-5 | O | CH | H | OCH₃ |
| b-6 | O | N | H | OCH₃ |
| b-7 | S | CH | H | OCH₃ |
| b-8 | S | N | H | OCH₃ |
| b-9 | O | CH | H | OCH₂CH₃ |
| b-10 | O | N | H | OCH₂CH₃ |
| b-11 | S | CH | H | OCH₂CH₃ |
| b-12 | S | N | H | OCH₂CH₃ |
| b-13 | O | CH | H | OCH₂CH₂CH₃ |
| b-14 | O | N | H | OCH₂CH₂CH₃ |
| b-15 | S | CH | H | OCH₂CH₂CH₃ |
| b-16 | S | N | H | OCH₂CH₂CH₃ |
| b-17 | O | CH | H | OCH₂CH₂CH₂CH₃ |
| b-18 | O | N | H | OCH₂CH₂CH₂CH₃ |
| b-19 | O | CH | H | OCH₂CH₂CH₂CH₂CH₃ |
| b-20 | O | N | H | OCH₂CH₂CH₂CH₂CH₃ |
| b-21 | O | CH | H | OCH₂CH=CH₂ |
| b-22 | O | N | H | OCH₂CH=CH₂ |
| b-23 | O | CH | H | OCH(CH₃)₂ |
| b-24 | O | N | H | OCH(CH₃)₂ |
| b-25 | O | CH | H | OCH₂C≡CH |
| b-26 | O | N | H | OCH₂C≡CH |
| b-27 | O | CH | H | O(c-C₅H₉) |
| b-28 | O | N | H | O(c-C₅H₉) |
| b-29 | O | CH | H | O(c-C₆H₁₁) |
| b-30 | O | N | H | O(c-C₆H₁₁) |
| b-31 | O | CH | H | OCH₂CO₂CH₃ |
| b-32 | O | N | H | OCH₂CO₂CH₃ |
| b-33 | O | CH | H | OC(CH₃)₂CO₂CH₃ |
| b-34 | O | N | H | OC(CH₃)₂CO₂CH₃ |
| b-35 | O | CH | H | NH₂ |
| b-36 | O | N | H | NH₂ |
| b-37 | S | CH | H | NH₂ |
| b-38 | S | N | H | NH₂ |
| b-39 | O | CH | H | NHCH₃ |
| b-40 | O | N | H | NHCH₃ |
| b-41 | S | CH | H | NHCH₃ |
| b-42 | S | N | H | NHCH₃ |
| b-43 | O | CH | H | NHCH₂CH₃ |
| b-44 | O | N | H | NHCH₂CH₃ |
| b-45 | S | CH | H | NHCH₂CH₃ |
| b-46 | S | N | H | NHCH₂CH₃ |
| b-47 | O | CH | H | NHCH₂CH₂CH₃ |
| b-48 | O | N | H | NHCH₂CH₂CH₃ |
| b-49 | S | CH | H | NHCH₂CH₂CH₃ |
| b-50 | S | N | H | NHCH₂CH₂CH₃ |
| b-51 | O | CH | H | NHCH₂CH₂CH₂CH₃ |
| b-52 | O | N | H | NHCH₂CH₂CH₂CH₃ |
| b-53 | O | CH | H | NHCH₂CH₂CH₂CH₂CH₃ |
| b-54 | O | N | H | NHCH₂CH₂CH₂CH₂CH₃ |
| b-55 | O | CH | H | NHCH₂CH=CH₂ |
| b-56 | O | N | H | NHCH₂CH=CH₂ |
| b-57 | O | CH | H | NHCH(CH₃)₂ |
| b-58 | O | N | H | NHCH(CH₃)₂ |
| b-59 | O | CH | H | NHCH₂C≡CH |
| b-60 | O | N | H | NHCH₂C≡CH |
| b-61 | O | CH | H | NH(c-C₅H₉) |
| b-62 | O | N | H | NH(c-C₅H₉) |
| b-63 | O | CH | H | NH(c-C₆H₁₁) |
| b-64 | O | N | H | NH(c-C₆H₁₁) |
| b-65 | O | CH | H | NHCH₂CO₂CH₃ |
| b-66 | O | N | H | NHCH₂CO₂CH₃ |
| b-67 | O | CH | H | NHC(CH₃)₂CO₂CH₃ |
| b-68 | O | N | H | NHC(CH₃)₂CO₂CH₃ |
| b-69 | NH | CH | H | OH |
| b-70 | NH | N | H | OH |
| b-71 | NH | CH | H | OH |
| b-72 | NH | N | H | OH |
| b-73 | NH | CH | H | OCH₃ |
| b-74 | NH | N | H | OCH₃ |
| b-75 | NH | CH | H | OCH₃ |
| b-76 | NH | N | H | OCH₃ |
| b-77 | NH | CH | H | OCH₂CH₃ |
| b-78 | NH | N | H | OCH₂CH₃ |
| b-79 | NH | CH | H | OCH₂CH₃ |
| b-80 | NH | N | H | OCH₂CH₃ |
| b-81 | NH | CH | H | OCH₂CH₂CH₃ |
| b-82 | NH | N | H | OCH₂CH₂CH₃ |
| b-83 | NH | CH | H | OCH₂CH₂CH₃ |
| b-84 | NH | N | H | OCH₂CH₂CH₃ |
| b-85 | NH | CH | H | OCH₂CH₂CH₂CH₃ |
| b-86 | NH | N | H | OCH₂CH₂CH₂CH₃ |
| b-87 | NH | CH | H | OCH₂CH₂CH₂CH₂CH₃ |
| b-88 | NH | N | H | OCH₂CH₂CH₂CH₂CH₃ |
| b-89 | NH | CH | H | OCH₂CH=CH₂ |
| b-90 | NH | N | H | OCH₂CH=CH₂ |
| b-91 | O | CH | H | ONHCH₃ |
| b-92 | O | N | H | ONHCH₃ |
| b-93 | O | CH | H | ONHCH₂CH₃ |
| b-94 | O | N | H | ONHCH₂CH₃ |
| b-95 | O | CH | H | ON(CH₃)₂ |
| b-96 | O | N | H | ON(CH₃)₂ |
| b-97 | O | CH | H | ON=C(CH₃)₂ |
| b-98 | O | N | H | ON=C(CH₃)₂ |
| b-99 | O | CH | H | N(CH₂CH₃)₂ |
| b-100 | O | N | H | N(CH₂CH₃)₂ |
| b-101 | O | CH | H | N(CH₃)(CH₂CH₃) |
| b-102 | O | N | H | N(CH₃)(CH₂CH₃) |
| b-103 | O | CH | H | NHOCH₃ |
| b-104 | O | N | H | NHOCH₃ |
| b-105 | O | CH | H | NHOCH₂CH₃ |
| b-106 | O | N | H | NHOCH₂CH₃ |
| b-107 | O | CH | 5-Cl | OCH₃ |
| b-108 | O | N | 5-Cl | OCH₃ |
| b-109 | S | CH | 5-Cl | OCH₃ |
| b-110 | S | N | 5-Cl | OCH₃ |
| b-111 | O | CH | 5-Cl | OCH₂CH₃ |
| b-112 | O | N | 5-Cl | OCH₂CH₃ |
| b-113 | O | CH | 5-F | OCH₃ |
| b-114 | O | N | 5-F | OCH₃ |
| b-115 | O | CH | 5-CH₃ | OCH₃ |
| b-116 | O | N | 5-CH₃ | OCH₃ |
| b-117 | O | CH | 5-OCH₃ | OCH₃ |
| b-118 | O | N | 5-OCH₃ | OCH₃ |
| b-119 | O | CH | 5-OCH₃ | OCH₂CH₃ |
| b-120 | O | N | 5-OCH₃ | OCH₂CH₃ |
| b-121 | O | CH | H | O-tert-C₄H₉ |
| b-122 | O | N | H | O-tert-C₄H₉ |

TABLE 2-continued

Compounds of formula (I-b) (compound b-1 to compound b-124)

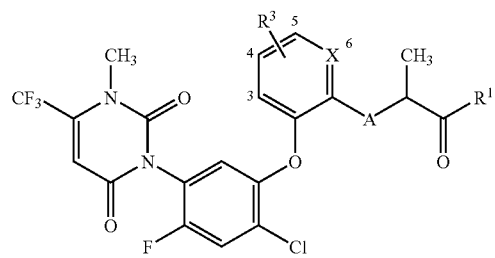

(I-b)

| Compound No. | A | X | R³ | R¹ |
|---|---|---|---|---|
| b-123 | O | CH | H | O-iso-C₄H₉ |
| b-124 | O | N | H | O-iso-C₄H₉ |

TABLE 3

Compounds of formula (I-c) (compound c-1 to compound c-48)

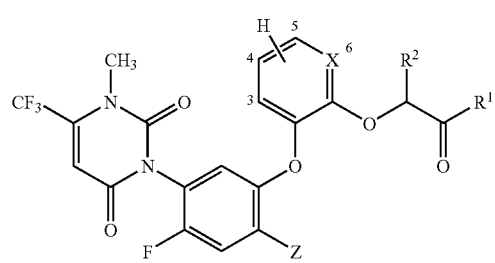

(I-c)

| Compound No. | Z | X | R² | R¹ |
|---|---|---|---|---|
| c-1 | Br | CH | H | OH |
| c-2 | Br | N | H | OH |
| c-3 | Br | CH | CH₃ | OH |
| c-4 | Br | N | CH₃ | OH |
| c-5 | Br | CH | H | OCH₃ |
| c-6 | Br | N | H | OCH₃ |
| c-7 | Br | CH | CH₃ | OCH₃ |
| c-8 | Br | N | CH₃ | OCH₃ |
| c-9 | Br | CH | H | OCH₂CH₃ |
| c-10 | Br | N | H | OCH₂CH₃ |
| c-11 | Br | CH | CH₃ | OCH₂CH₃ |
| c-12 | Br | N | CH₃ | OCH₂CH₃ |
| c-13 | Br | CH | H | OCH₂CH₂CH₃ |
| c-14 | Br | N | H | OCH₂CH₂CH₃ |
| c-15 | Br | CH | CH₃ | OCH₂CH₂CH₃ |
| c-16 | Br | N | CH₃ | OCH₂CH₂CH₃ |
| c-17 | Br | CH | H | OCH₂CH₂CH₂CH₂CH₃ |
| c-18 | Br | N | H | OCH₂CH₂CH₂CH₂CH₃ |
| c-19 | Br | CH | CH₃ | OCH₂CH₂CH₂CH₂CH₃ |
| c-20 | Br | N | CH₃ | OCH₂CH₂CH₂CH₂CH₃ |
| c-21 | Br | CH | H | O(c-C₅H₉) |
| c-22 | Br | N | H | O(c-C₅H₉) |
| c-23 | Br | CH | CH₃ | O(c-C₅H₉) |
| c-24 | Br | N | CH₃ | O(c-C₅H₉) |
| c-25 | F | CH | H | OCH₃ |
| c-26 | F | N | H | OCH₃ |
| c-27 | F | CH | CH₃ | OCH₃ |
| c-28 | F | N | CH₃ | OCH₃ |
| c-29 | F | CH | H | OCH₂CH₃ |
| c-30 | F | N | H | OCH₂CH₃ |
| c-31 | F | CH | CH₃ | OCH₂CH₃ |
| c-32 | F | N | CH₃ | OCH₂CH₃ |
| c-33 | F | CH | H | OCH₂CO₂CH₃ |
| c-34 | F | N | H | OCH₂CO₂CH₃ |
| c-35 | F | CH | H | OC(CH₃)₂CH₂CH₃ |
| c-36 | F | N | H | OC(CH₃)₂CO₂CH₃ |
| c-37 | I | CH | H | OCH₃ |
| c-38 | I | N | H | OCH₃ |
| c-39 | O | CH | CH₃ | OCH₃ |
| c-40 | I | N | CH₃ | OCH₃ |
| c-41 | O | CH | H | OCH₂CH₃ |
| c-42 | O | N | H | OCH₂CH₃ |
| c-43 | I | CH | CH₃ | OCH₂CH₃ |
| c-44 | I | N | CH₃ | OCH₂CH₃ |
| c-45 | Br | CH | H | NH₂ |
| c-46 | Br | N | H | NH₂ |
| c-47 | Br | CH | H | NHCH₃ |
| c-48 | Br | N | H | NHCH₃ |

The following will describe formulation examples. In these formulation examples, "parts" represents parts by weight.

FORMULATION EXAMPLE 1

Fifty parts of each of compounds a-1 to a-124, compounds b-1 to b-124, and compounds c-1 to c-48, 3 parts of calcium lignin sulfonate, 2 parts of sodium lauryl sulfate, and 45 parts of synthetic hydrated silicon oxide are well pulverized and mixed to give a wettable powder for each compound.

FORMULATION EXAMPLE 2

Seventy parts of each of compounds a-1 to a-124, compounds b-1 to b-124, and compounds c-1 to c-48, 3 parts of calcium lignin sulfonate, 2 parts of sodium lauryl sulfate, and 25 parts of synthetic hydrated silicon oxide are well pulverized and mixed to give a wettable powder for each compound.

FORMULATION EXAMPLE 3

Twenty parts of each of compounds a-1 to a-124, compounds b-1 to b-124, and compounds c-1 to c-48, 3 parts of polyoxyethylene sorbitan monooleate, 3 parts of CMC (carboxymethylcellulose), and 74 parts of water are mixed and wet pulverized so that the mean particle size comes to 5 μm or smaller to give a flowable of each compound.

FORMULATION EXAMPLE 4

Forty parts of each of compounds a-i to a-124, compounds b-1 to b-124, and compounds c-1 to c-48, 3 parts of polyoxyethylene sorbitan monooleate, 3 parts of CMC (carboxymethylcellulose), and 54 parts of water are mixed and wet pulverized so that the mean particle size comes to 5 μm or smaller to give a flowable of each compound.

The following will describe test example and the present invention should not be limited to the test example.

The test results were evaluated according to the following criteria:

Defoliation ratio (%)=(the number of dropped leaves/the total number of leaves examined)× 100

TEST EXAMPLE

Cotton seeds were planted and grown in the field. At the time of cotton boll opening, 2.5 parts of each of compounds a-6 and a-6, 10 parts of Sorpol 3890 (Toho Chemical Industry Co., Ltd.), and 87.5 parts of SOLVESSO 200 (Exxon Mobile Chemical Company) were well mixed to give an emulsifiable concentrate for each compound, which was then diluted at a prescribed dose with water containing 1% (v/v) crop oil concentrate (COC), and the dilution was uniformly sprayed to the plants. Treatments were carried out with three replications. Replication 1 had about 60% of open bolls; replication 2 had about 60 to 70% of open bolls; replication 3 had 80 to 85% of open boils. The treated fields are each 4 m×6.4 m in area, and the cotton plants on day 14 after the treatment were examined for the defoliation ratio. The results are shown in Table 4.

TABLE 4

| Test compound | Application rates (g/ha) | Defoliation ratio (%) Rep. 1 | Rep. 2 | Rep. 3 |
|---|---|---|---|---|
| Non-treated field | — | 0 | 0 | 0 |
| Compound a-5 | 20 | 85 | 90 | 82 |
| Compound a-6 | 20 | 80 | 75 | 85 |

Each of the compounds a-5 and a-6 stimulated cotton boll opening.

INDUSTRIAL APPLICABILITY

The use of plant growth regulators for cotton harvest according to the present invention enables sufficient leaf drop of cotton plants and stimulates cotton boll opening, so that harvest works can easily be performed with high efficiency.

The invention claimed is:

1. A method of regulating plant growth for cotton harvest, which comprises applying as an active ingredient, a compound of formula (I):

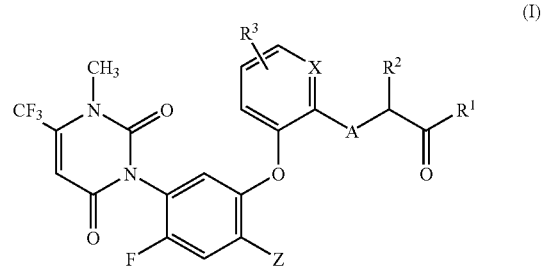

wherein X is CH or nitrogen; Z is halogen; A is oxygen, sulfur, or NH; $R^1$ is hydroxyl, $C_1$–$C_7$ alkoxy, $C_3$–$C_7$ alkenyloxy, $C_3$–$C_7$ alkynyloxy, $C_5$–$C_7$ cycloalkoxy, $\{(C_1$–$C_7$ alkoxy)carbonyl\}$C_1$–$C_3$ alkoxy, ($C_1$–$C_7$ alkylamino)oxy, {di($C_1$–$C_7$ alkyl)amino}oxy, ($C_3$–$C_7$ alkylideneamino)oxy, $C_1$–$C_7$ alkylamino, di($C_1$–$C_7$ alkyl)amino, $C_3$–$C_7$ alkenylamino, $C_3$–$C_7$ alkynylamino, $C_5$–$C_7$ cycloalkylamino, $\{(C_1$–$C_7$ alkoxy)carbonyl\}$C_1$–$C_3$ alkylamino, or ($C_1$–$C_7$ alkoxy)amino; $R^2$ is hydrogen or methyl; and $R^3$ is hydrogen, halogen, $C_1$–$C_3$ alkyl, or $C_1$–$C_3$ alkoxy,
to parts of cotton plants that are above the ground, prior to cotton harvest.

2. A method for defoliating cotton plants, which comprises applying a compound of formula (I) according to claim 1 to parts of cotton plants that are above the ground, prior to cotton harvest.

3. A method for stimulating cotton ball openings, which comprises applying a compound of formula (I) according to claim 1 to parts of cotton plants that are above the ground, prior to cotton harvest.

4. The method according to any one of claims 2 and 3, wherein the application is carried out at the time of cotton boll opening.

5. The method according to any one of claims 2 and 3, wherein the compound of formula (I) is applied in an amount of 1 to 500 g/ha.

6. The method according to claim 4, wherein the compound of formula (I) is applied in an amount of 1 to 500 g/ha.

* * * * *